United States Patent
Chen et al.

(10) Patent No.: US 11,951,216 B2
(45) Date of Patent: *Apr. 9, 2024

(54) POLYMER PROTEIN MICROPARTICLES

(71) Applicant: Regeneron Pharmaceuticals, Inc., Tarrytown, NY (US)

(72) Inventors: Hunter Chen, New York, NY (US); Scott Walsh, Tarrytown, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 47 days.

This patent is subject to a terminal disclaimer.

(21) Appl. No.: 17/677,282

(22) Filed: Feb. 22, 2022

(65) Prior Publication Data

US 2022/0249387 A1 Aug. 11, 2022

Related U.S. Application Data

(60) Continuation of application No. 15/450,335, filed on Mar. 6, 2017, now Pat. No. 11,291,636, which is a division of application No. 13/680,069, filed on Nov. 18, 2012, now abandoned.

(60) Provisional application No. 61/561,525, filed on Nov. 18, 2011.

(51) Int. Cl.
| | | |
|---|---|---|
| *A61K 9/50* | (2006.01) | |
| *A61K 9/14* | (2006.01) | |
| *A61K 9/16* | (2006.01) | |
| *A61K 38/17* | (2006.01) | |
| *A61P 27/02* | (2006.01) | |

(52) U.S. Cl.
CPC .............. *A61K 9/5089* (2013.01); *A61K 9/14* (2013.01); *A61K 9/1611* (2013.01); *A61K 9/1617* (2013.01); *A61K 9/1623* (2013.01); *A61K 9/5031* (2013.01); *A61K 9/5047* (2013.01); *A61K 38/179* (2013.01); *A61P 27/02* (2018.01); *A61K 9/1641* (2013.01); *A61K 9/1647* (2013.01); *A61K 9/1652* (2013.01)

(58) Field of Classification Search
CPC ...... A61K 9/5089; A61K 9/14; A61K 9/1611; A61K 9/1617; A61K 9/1623; A61K 9/5031; A61K 9/5047; A61K 38/179; A61K 9/1641; A61K 9/1647; A61K 9/1652; A61K 2039/505; A61K 38/00; A61K 47/34; A61K 47/36; A61P 27/02
See application file for complete search history.

(56) References Cited

U.S. PATENT DOCUMENTS

| | | |
|---|---|---|
| 4,210,529 A | 7/1980 | Petersen |
| 4,304,767 A | 12/1981 | Heller et al. |
| 4,764,364 A | 8/1988 | Heller et al. |
| 5,104,221 A | 4/1992 | Bott et al. |
| 5,968,543 A | 10/1999 | Heller et al. |
| 5,985,309 A | 11/1999 | Edwards et al. |
| 6,004,549 A | 12/1999 | Reichert et al. |
| 6,011,011 A | 1/2000 | Hageman |
| 6,019,968 A | 2/2000 | Platz et al. |
| 6,063,910 A | 5/2000 | Debenedetti et al. |
| 6,284,282 B1 | 9/2001 | Maa et al. |
| 6,308,434 B1 | 10/2001 | Chickering, III et al. |
| 6,927,004 B2 | 8/2005 | Eurlings et al. |
| 6,927,044 B2 | 8/2005 | Stahl et al. |
| 6,956,021 B1 | 10/2005 | Edwards et al. |
| 7,087,411 B2 | 8/2006 | Daly et al. |
| 7,279,158 B2 | 10/2007 | Wang et al. |
| 7,279,159 B2 | 10/2007 | Daly et al. |
| 7,303,746 B2 | 12/2007 | Wiegand et al. |
| 7,303,747 B2 | 12/2007 | Wiegand et al. |
| 7,365,165 B2 | 4/2008 | Dix et al. |
| 7,374,758 B2 | 5/2008 | Papadopoulos et al. |
| 7,572,893 B2 | 8/2009 | Dix et al. |
| 7,608,261 B2 | 10/2009 | Furfine et al. |
| 7,655,758 B2 | 2/2010 | Dix et al. |
| 7,807,164 B2 | 10/2010 | Furfine et al. |
| 7,927,583 B2 | 4/2011 | Stahl et al. |
| 7,998,477 B2 | 8/2011 | Yakovlevsky et al. |
| 8,063,182 B1 | 11/2011 | Brockhaus et al. |
| 8,173,599 B2 | 5/2012 | Moon et al. |
| 8,586,713 B2 | 11/2013 | Davis et al. |
| 8,623,395 B2 | 1/2014 | de Juan, Jr. et al. |
| 9,033,911 B2 | 5/2015 | de Juan, Jr. et al. |
| 9,155,702 B2 | 10/2015 | Lee et al. |
| 9,376,479 B2 | 6/2016 | Govardhan et al. |
| 9,610,301 B2 | 4/2017 | Lassner et al. |
| 10,611,850 B2 | 4/2020 | Christian et al. |
| 2004/0043076 A1 | 3/2004 | Dulieu et al. |
| 2004/0142043 A1 | 7/2004 | Maeda et al. |

(Continued)

FOREIGN PATENT DOCUMENTS

| | | |
|---|---|---|
| AU | 2012340107 A1 | 6/2014 |
| AU | 2016340072 A1 | 5/2018 |

(Continued)

OTHER PUBLICATIONS

U.S. Appl. No. 13/680,069, filed Nov. 18, 2012, Abandoned.
U.S. Appl. No. 15/450,335, filed Mar. 6, 2017, Issued.
Hollenbaugh et al., Construction of Immunoglobulin Fusion Proteins. Current Protocols in Immunology. 2002;48:10.19A.1-10.19A.11.

(Continued)

*Primary Examiner* — Sarah Alawadi
*Assistant Examiner* — Thurman Wheeler
(74) *Attorney, Agent, or Firm* — McCarter & English, LLP

(57) ABSTRACT

Microparticles containing a core of therapeutic protein and a cortex of a biocompatible and biodegradable polymer, and methods of making and using the microparticles are provided. The extended release of a therapeutic protein from the microparticles in a physiological solution is demonstrated over an extended period of time.

20 Claims, 3 Drawing Sheets

Figure 1:
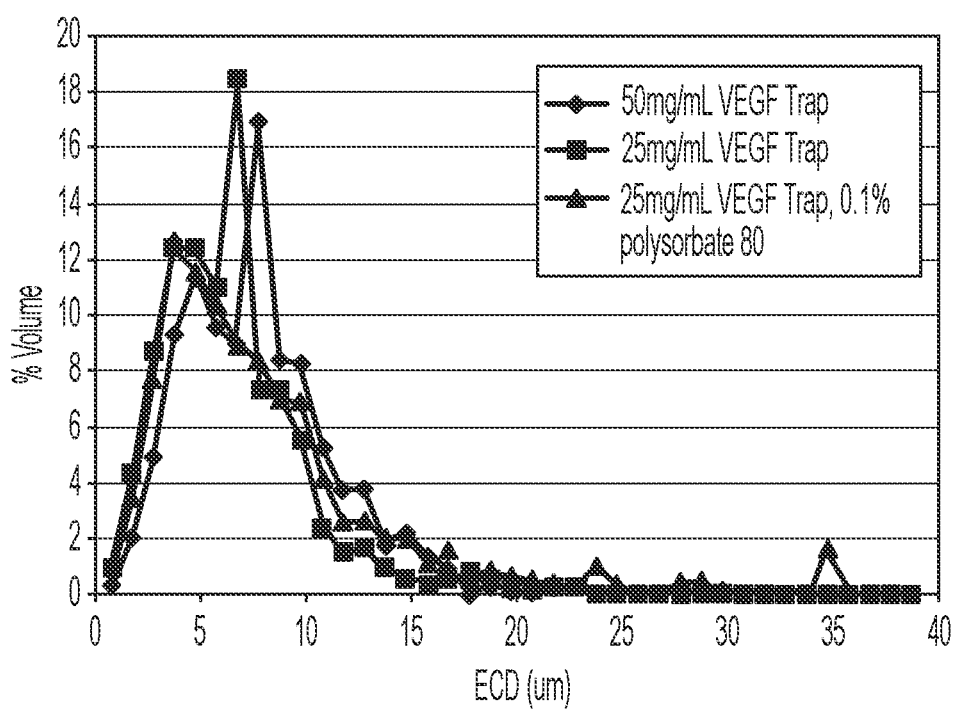

Specification includes a Sequence Listing.

(56) References Cited

U.S. PATENT DOCUMENTS

| | | |
|---|---|---|
| 2004/0208928 A1 | 10/2004 | Liao et al. |
| 2004/0209804 A1 | 10/2004 | Govardhan et al. |
| 2004/0219224 A1 | 11/2004 | Yakovlevsky et al. |
| 2005/0175708 A1 | 8/2005 | Carrasquillo et al. |
| 2005/0186143 A1 | 8/2005 | Stevenson et al. |
| 2005/0250704 A1 | 11/2005 | Bassarab et al. |
| 2005/0281861 A1 | 12/2005 | Hughes et al. |
| 2006/0210641 A1 | 9/2006 | Shalaby |
| 2007/0059336 A1 | 3/2007 | Hughes et al. |
| 2007/0071825 A1 | 3/2007 | Curdy et al. |
| 2007/0264341 A1 | 11/2007 | Lee et al. |
| 2007/0292475 A1 | 12/2007 | Campbell et al. |
| 2007/0298116 A1 | 12/2007 | Bechtold-Peters et al. |
| 2008/0071064 A1 | 3/2008 | Schultz-Fademrecht et al. |
| 2008/0305115 A1 | 12/2008 | Tice et al. |
| 2009/0226530 A1 | 9/2009 | Lassner et al. |
| 2009/0269414 A1 | 10/2009 | Lee et al. |
| 2010/0279933 A1 | 11/2010 | Dix et al. |
| 2011/0046870 A1 | 2/2011 | Ross et al. |
| 2011/0104151 A1 | 5/2011 | Nettles et al. |
| 2011/0171241 A1 | 7/2011 | Dix et al. |
| 2011/0212180 A1 | 9/2011 | Ramtoola |
| 2012/0095439 A1 | 4/2012 | de Juan, Jr. et al. |
| 2013/0129830 A1 | 5/2013 | Chen et al. |
| 2013/0324942 A1 | 12/2013 | de Juan, Jr. et al. |
| 2014/0170204 A1 | 6/2014 | Desai et al. |
| 2014/0363482 A1 | 12/2014 | Guo et al. |
| 2015/0119807 A1 | 4/2015 | Desai et al. |
| 2015/0216829 A1 | 8/2015 | Conte et al. |
| 2015/0250647 A1 | 9/2015 | de Juan, Jr. et al. |
| 2016/0030553 A1 | 2/2016 | Legon |
| 2016/0176986 A1 | 6/2016 | Armstrong et al. |
| 2017/0181978 A1 | 6/2017 | Chen et al. |
| 2017/0198058 A1 | 7/2017 | Christian et al. |
| 2018/0289623 A1 | 10/2018 | Chen et al. |
| 2020/0022917 A1 | 1/2020 | Brudnicki et al. |

FOREIGN PATENT DOCUMENTS

| | | |
|---|---|---|
| AU | 2016369557 A1 | 6/2018 |
| BR | 112014011915 A2 | 5/2017 |
| BR | 112018007507 A2 | 10/2018 |
| BR | 112018010743 A2 | 11/2018 |
| CA | 2710062 A1 | 7/2009 |
| CA | 2711984 A1 | 7/2009 |
| CA | 2855749 A1 | 5/2013 |
| CA | 3076725 A1 | 5/2013 |
| CA | 3001346 A1 | 4/2017 |
| CA | 3003654 A1 | 6/2017 |
| CL | 2018001623 A1 | 7/2018 |
| CN | 1222403 A | 7/1999 |
| CN | 101132800 A | 2/2008 |
| CN | 101559041 A | 10/2009 |
| CN | 102365109 A | 2/2012 |
| CN | 103108656 A | 5/2013 |
| CN | 103209664 A | 7/2013 |
| CN | 103717237 A | 4/2014 |
| CN | 103957898 A | 7/2014 |
| CN | 105688188 A | 6/2016 |
| CN | 108348462 A | 7/2018 |
| CN | 108366968 A | 8/2018 |
| CO | 2018005920 A2 | 6/2018 |
| DE | 102006030164 A1 | 1/2008 |
| DK | 2790681 T3 | 4/2020 |
| DK | 3384903 T3 | 7/2020 |
| EA | 201890979 A1 | 10/2018 |
| EA | 201891164 A1 | 11/2018 |
| EP | 2790681 A1 | 10/2014 |
| EP | 3362041 A1 | 8/2018 |
| EP | 3384903 A1 | 10/2018 |
| EP | 3389636 A1 | 10/2018 |
| EP | 3574897 A1 | 12/2019 |
| ES | 2775104 T3 | 7/2020 |
| HK | 1251461 A1 | 2/2019 |
| IL | 258570 | 5/2018 |
| IL | 259204 | 7/2018 |
| IL | 232328 A | 11/2018 |
| IL | 262651 A | 11/2020 |
| JP | H08-501305 A | 2/1996 |
| JP | H11-228389 A | 8/1999 |
| JP | 2004-285079 A | 10/2004 |
| JP | 2010-522743 A | 7/2010 |
| JP | 2014-533698 A | 12/2014 |
| JP | 2017-525679 A | 9/2017 |
| JP | 6267649 B2 | 1/2018 |
| JP | 2018-141004 A | 9/2018 |
| JP | 2018-538243 A | 12/2018 |
| JP | 2019-504825 A | 2/2019 |
| JP | 6549653 B2 | 7/2019 |
| JP | 6727372 B2 | 7/2020 |
| KR | 10-2003-0011858 A | 2/2003 |
| KR | 10-2009-0025373 A | 3/2009 |
| KR | 10-2018-0063311 A | 6/2018 |
| KR | 10-2018-0088836 A | 8/2018 |
| KR | 2020-0018712 A | 2/2020 |
| KR | 10-2133352 B1 | 7/2020 |
| MX | 2018005382 A | 8/2018 |
| MX | 2018005383 A | 8/2018 |
| MX | 2018005384 A | 8/2018 |
| MX | 2018005387 A | 8/2018 |
| MX | 2018005388 A | 8/2018 |
| MX | 2018005390 A | 8/2018 |
| MX | 362286 B | 1/2019 |
| MX | 2018004695 A | 3/2019 |
| PH | 12018500830 A1 | 10/2018 |
| PT | 3384903 T | 6/2020 |
| RU | 2177785 C2 | 1/2002 |
| RU | 2237471 C2 | 10/2004 |
| RU | 2014124682 A | 12/2015 |
| RU | 2018101248 A | 2/2019 |
| SG | 11201402152 | 6/2014 |
| SG | 11201803197 U | 5/2018 |
| WO | WO-1992/018164 A1 | 10/1992 |
| WO | WO-1996/18417 A1 | 6/1996 |
| WO | WO-1999/038536 A1 | 8/1999 |
| WO | WO-2001/030320 A1 | 5/2001 |
| WO | WO-2003/092665 A2 | 11/2003 |
| WO | WO-2007/084765 A2 | 7/2007 |
| WO | WO-2008/109886 A1 | 9/2008 |
| WO | WO-2008/115883 A1 | 9/2008 |
| WO | WO-2008/153997 A1 | 12/2008 |
| WO | WO-2009/090189 A1 | 7/2009 |
| WO | WO-2010/111132 A2 | 9/2010 |
| WO | WO-2011/041642 A1 | 4/2011 |
| WO | 2012/047954 A1 | 4/2012 |
| WO | WO-2012/142318 A1 | 10/2012 |
| WO | WO-2013/075068 A1 | 5/2013 |
| WO | WO-2017/066554 A1 | 4/2017 |
| WO | WO-2017/106716 A1 | 6/2017 |
| ZA | 201800078 B | 5/2020 |

OTHER PUBLICATIONS

Sharma et al., Micro-flow imaging: flow microscopy applied to sub-visible particulate analysis in protein formulations. AAPS J. Sep. 2010;12(3):455-64.

European Office Action for Application No. 22150172.9, dated May 27, 2022, 17 pages.

Abdul-Fattah et al., The Challenge of Drying Method Selection for Protein Pharmaceuticals: Product Quality Implications. J Pharm Sci. Aug. 2007;96(8):1886-916.

Ajmera et al., Stabilisation of proteins via mixtures of amino acids during spray drying. Int J Pharm. Mar. 10, 2014;463(1):98-107.

Ajmera, Stable spray dried protein formulation and implementation in vaccine development. Doctoral thesis, Christian Albrecht University, Kiel, Germany, 140 pages. (2014).

Albin et al., Theoretical and experimental studies of glucose sensitive membranes. J Control Rel. 1987;6:267-91.

Andrieu-Soler et al., Intravitreous injection of PLGA microspheres encapsulating GDNF promotes the survival of photoreceptors in the rd1/rd1 mouse. Mol Vis. Nov. 17, 2005;11:1002-11.

(56) References Cited

OTHER PUBLICATIONS

Arpagaus et al., Spray dried biodegradable polymers as target material for controlled drug delivery. Best@buchi. vol. 46, 8 pages, (2007).
Arthur et al., Detection of protein aggregates by sedimentation velocity analytical ultracentrifugation (SV-AUC): sources of variability and their relative importance. J Pharm Sci. Oct. 2009;98(10):3522-39.
Ashkenazi et al., Protection against endotoxic shock by a tumor necrosis factor receptor immunoadhesin. Proc Natl Acad Sci U S A. Dec. 1, 1991;88(23):10535-9.
Astete et al., Synthesis and characterization of PLGA nanoparticles. J Biomater Sci Polym Ed. 2006;17(3):247-89.
Atha et al., Mechanism of precipitation of proteins by polyethylene glycols. Analysis in terms of excluded volume. J Biol Chem. Dec. 10, 1981;256(23):12108-17.
Bauman et al., Antagonism of platelet-derived growth factor receptor in non small cell lung cancer: rationale and investigations. Clin Cancer Res. Aug. 1, 2007;13(15 Pt 2):s4632-6.
Bernards et al., Nanostructured thin film polymer devices for constant-rate protein delivery. Nano Lett. Oct. 10, 2012;12(10):5355-61.
Bernards et al., Ocular biocompatibility and structural integrity of micro- and nanostructured poly(caprolactone) films. J Ocul Pharmacol Ther. Mar. 2013;29(2):249-57.
Bhambhani et al., Formulation design and high-throughput excipient selection based on structural integrity and conformational stability of dilute and highly concentrated IgG1 monoclonal antibody solutions. J Pharm Sci. Mar. 2012;101(3):1120-35. (Abstract only).
Blixt et al., Arraying the post-translational glycoproteome (PTG). Curr Opin Chem Biol. Feb. 2014;18:62-9.
Broadhead et al., The effect of process and formulation variables on the properties of spray-dried beta-galactosidase. J Pharm Pharmacol. Jun. 1994;46(6):458-67.
Brown et al., Primary endpoint results of a phase II study of vascular endothelial growth factor trap-eye in wet age-related macular degeneration. Ophthalmology. Jun. 2011;118(6):1089-97.
Burke et al., Poly(lactide-co-glycolide) microsphere formulations of darbepoetin alfa: spray drying is an alternative to encapsulation by spray-freeze drying. Pharm Res. Mar. 2004;21(3):500-6.
Bustami et al., Generation of micro-particles of proteins for aerosol delivery using high pressure modified carbon dioxide. Pharm Res. Nov. 2000;17(11):1360-6.
Butler et al., The choice of mammalian cell host and possibilities for glycosylation engineering. Curr Opin Biotechnol. Dec. 2014;30:107-12.
Byrn et al., Biological properties of a CD4 immunoadhesin. Nature. Apr. 12, 1990;344(6267):667-70.
Chen et al., Profiling glycoprotein n-linked oligosaccharide by capillary electrophoresis. Electrophoresis. Nov. 1998;19(15):2639-44. (Abstract only).
Cleland et al., A specific molar ratio of stabilizer to protein is required for storage stability of a lyophilized monoclonal antibody. J Pharm Sci. Mar. 2001;90(3):310-21.
Costantino et al., Effect of mannitol crystallization on the stability and aerosol performance of a spray-dried pharmaceutical protein, recombinant humanized anti-IgE monoclonal antibody. J Pharm Sci. Nov. 1998;87(11):1406-11.
De Boer et al., Characterization of inhalation aerosols: a critical evaluation of cascade impactor analysis and laser diffraction technique. Int J Pharm. Dec. 5, 2002;249(1-2):219-31.
Do et al., The Da Vinci Study: phase 2 primary results of VEGF Trap-Eye in patients with diabetic macular edema. Ophthalmology. Sep. 2011;118(9):1819-26.
Doat et al., Intravitreous injection of PLGA microspheres encapsulating GDNF promotes the survival of photoreceptors in the rd1/rd1 mouse. Mol Vis. 2005;11:1002-11.
Elversson et al., Aqueous two-phase systems as a formulation concept for spray-dried protein. Int J Pharm. Apr. 27, 2005;294(1-2):73-87.
Erdinc, Encapsulation of proteins by spray drying. Queen's University, Canada. 2007;1-89.
Fischer et al., Average protein density is a molecular-weight-dependent function. Protein Science. 2004;13:2825-8.
Frisken, Revisiting the method of cumulants for the analysis of dynamic light-scattering data. Appl Opt. Aug. 20, 2001;40(24):4087-91.
Gavini et al., PLGA microspheres for the occular delivery of a peptide drug, vancomycin using emulsification/spray-drying as the preparation method: in vitro/in vivo studies. Eur J Pharm Biopharm. 2004;57(2):207-12.
Gerald et al., Angiopoietin-2: an attractive target for improved antiangiogenic tumor therapy. Cancer Res. Mar. 15, 2013;73(6):1649-57.
Ghaderi et al., Production platforms for biotherapeutic glycoproteins. Occurrence, impact, and challenges of non-human sialylation. Biotechnol Genet Eng Rev. 2012;28:147-75.
Gibas et al., Review: synthetic polymer hydrogels for biomedical applications. Chemistry and Chemical Technology. 2010;4:297-304.
Gikanga et al., Manufacturing of High-Concentration Monoclonal Antibody Formulations via Spray Drying—the Road to Manufacturing Scale. PDA J Pharm Sci Technol. Jan.-Feb. 2015;69(1):59-73.
Gin et al., Chemistry. Designing the next generation of chemical separation membranes. Science. May 6, 2011;332(6030):674-6.
Goldberg et al., Formulation development of therapeutic monoclonal antibodies using high-throughput fluorescence and static light scattering techniques: role of conformational and colloidal stability. J Pharm Sci. Apr. 2011;100(4):1306-15.
He et al., Use of a nanoporous biodegradable miniature device to regulate cytokine release for cancer treatment. J Control Release. May 10, 2011;151(3):239-45.
Heier et al., The 1-year Results of CLEAR-IT 2, a Phase 2 Study of Vascular Endothelial Growth Factor Trap-Eye Dosed As-needed After 12-week Fixed Dosing. Ophthalmology. 2011;118(6):1098-106.
Heier, VEGF Trap-Eye for Exudative AMD. Retinal Physician. Apr. 2009;1-7.
Heller et al., Poly(ortho esters)—from concept to reality. Biomacromolecules. Sep.-Oct. 2004;5(5):1625-32.
Heller et al., Poly(ortho esters): synthesis, characterization, properties and uses. Adv Drug Deliv Rev. Oct. 16, 2002;54(7):1015-39.
Heller, Ocular delivery using poly(ortho esters), Adv Drug Deliv Rev. Dec. 13, 2005;57(14):2053-62.
Herrmann et al., New insight into the role of polyethylene glycol acting as protein release modifier in lipidic implants. Pharm Res. Aug. 2007;24(8):1527-37.
Hoe et al., Manufacturing and device options for the delivery of biotherapeutics. J Aerosol Med Pulm Drug Deliv. Oct. 2014;27(5):315-28.
Holash et al., VEGF-Trap: a VEGF blocker with potent antitumor effects. Proc Natl Acad Sci U S A. Aug. 20, 2002;99(17):11393-8.
Huang, Receptor-Fc fusion therapeutics, traps, and MIMETIBODY technology. Curr Opin Biotechnol. Dec. 2009;20(6):692-9.
Ishihara et al., Glucose Induced Permeation Control of Insulin through a Complex Membrane Consisting of Immobilized Glucose Oxidase and a Poly(amine). Polymer J. 1984;16(8):625-31.
Jain et al., Controlled drug delivery by biodegradable poly(ester) devices: different preparative approaches. Drug Dev Ind Pharm. Aug. 1998;24(8):703-27.
Jakubke et al., Amino acids, peptides, proteins. M: Mir. 1985:92-4.
Jezek et al., Viscosity of concentrated therapeutic protein compositions. Adv Drug Deliv Rev. Oct. 2011;63(13):1107-17.
Johnson et al., A month-long effect from a single injection of microencapsulated human growth hormone. Nat Med. Jul. 1996;2(7):795-9.
Joubert et al., Classification and characterization of therapeutic antibody aggregates. J Biol Chem. Jul. 15, 2011;286(28):25118-33.
Kim et al., BSA-FITC-loaded microcapsules for in vivo delivery. Biomaterials. Feb. 2009;30(5):902-9.

(56) References Cited

OTHER PUBLICATIONS

Kono et al., Adding to the Mix: Fibroblast Growth Ffactor and Platelet-Derived Growth Factor Receptor Pathways as Targets in Non-Small Cell Lung Cancer. Curr Cancer Drug Targets. Feb. 2012;12(2):107-23.
Kost et al., Glucose-sensitive membranes containing glucose oxidase: activity, swelling, and permeability studies. J Biomed Mater Res. Nov.-Dec. 1985;19(9):1117-33.
Labet et al., Synthesis of polycaprolactone: a review. Chem Soc Rev. Dec. 2009;38(12):3484-504.
Lance et al., In vivo and in vitro sustained release of ranibizumab from a nanoporous thin-film device. Drug Deliv Transl Res. Dec. 2016;6(6):771-780.
Lechuga-Ballesteros et al., Trileucine improves aerosol performance and stability of spray-dried powders for inhalation. J Pharm Sci. Jan. 2008;97(1):287-302.
Lee et al., In vivo characterization of sustained-release formulations of human growth hormone. J Pharmacol Exp Ther. Jun. 1997;281(3):1431-9.
Lee et al., Nano spray drying: A novel method for preparing protein nanoparticles for protein therapy. Int J Pharm. Jan. 17, 2011;403(1-2):192-200.
Li et al., Preparation and characterization of chitosan nanopores membranes for the transport of drugs. Int J Pharm. Nov. 28, 2011;420(2):371-7.
Mahadevan et al., Statistical-mechanical model of protein precipitation by nonionic polymer. AIChE Journal. 1990;36(10):1517-28.
Mahadevan et al., Theory of precipitation of protein mixtures by nonionic polymer. AIChE Journal. 1992;38(4):573-91.
Martinac et al., Spray-dried chitosan/ethylcellulose microspheres for nasal drug delivery: swelling study and evaluation of in vitro drug release properties. J Microencapsul. Aug. 2005;22(5):549-61.
Mercier et al., Organic polymers and ceramics. Introduction to Materials Science, Chapter 5. 2002;89-119.
Mordenti et al., Intraocular pharmacokinetics and safety of a humanized monoclonal antibody in rabbits after intravitreal administration of a solution or a PLGA microsphere formulation. Toxicol Sci. Nov. 1999;52(1):101-6.
Morita et al., Formation and isolation of spherical fine protein microparticles through lyophilization of protein-poly(ethylene glycol) aqueous mixture. Pharm Res. Nov. 2000;17(11):1367-73.
Mowen et al., Unconventional post-translational modifications in immunological signaling. Nat Immunol. Jun. 2014;15(6):512-20.
Nguyen et al., Protein powders for encapsulation: a comparison of spray-freeze drying and spray drying of darbepoetin alfa. Pharm Res. 2004;21:507-14.
Odaka et al., Ligand-binding enhances the affinity of dimerization of the extracellular domain of the epidermal growth factor receptor1. J Biochem. 1997;122:116-121. (Abstract Only).
Oka et al., Forming disulfides in the endoplasmic reticulum. Biochim Biophys Acta. Nov. 2013;1833(11):2425-9.
Pan et al., Comparison of long-acting bevacizumab formulations in the treatment of choroidal neovascularization in a rat model. J Ocul Pharmacol Ther. Jun. 2011;27(3):219-24.
Papadopoulos et al., Binding and neutralization of vascular endothelial growth factor (VEGF) and related ligands by VEGF Trap, ranibizumab and bevacizumab. Angiogenesis. Jun. 2012;15(2):171-85.
Philo, Is any measurement method optimal for all aggregate sizes and types? AAPS J. Sep. 8, 2006;8(3):E564-71.
Plomp et al., Recent advances in clinical glycoproteomics of immunoglobulins (Igs). Mol Cell Proteomics. 2016;15:2217-28. (Abstract Only).
Polson et al., The franctionation of protein mixtures by linear polymers of high molecular weight. Biochim Biophys Acta. 1964;82:463-75.
Regeneron, Eyelea Prescribing information. Regeneron Pharmaceuticals, Inc. pp. 1-15. (2011).
Ruth et al., alpha-L-iduronidase forms semi-crystalline spherulites with amyloid-like properties. Acta Crystallogr D Biol Crystallogr. Apr. 2000;56(Pt 4):524-8.
Safety data sheet (SDS) Methylene Chloride, Sankyo Chemical Co., Ltd. 2017, 22 pages.
Savage et al., Determination of adequate moisture content for efficient dry-heat viral inactivation in lyophilized factor VIII by loss on drying and by near infrared spectroscopy. Biologicals. Jun. 1998;26(2):119-24. (Abstract only).
Schlesinger et al., A Tunable, Biodegradable, Thin-Film Polymer Device as a Long-Acting Implant Delivering Tenofovir Alafenamide Fumarate for HIV Pre-exposure Prophylaxis. Pharm Res. Jul. 2016;33(7):1649-56.
Schule et al., Conformational analysis of protein secondary structure during spray-drying of antibody/mannitol formulations. Eur J Pharm Biopharm. 2007;65:1-9.
Schule et al., Stabilization of IgG1 in spray-dried powders for inhalation. Eur J Pharm Biopharm. 2008;69:793-807.
Sharma et al., Polyethylene glycol-induced precipitation of interferon Alpha-2a followed by vacuum drying: development of a novel process for obtaining a dry, stable powder. AAPS Pharm Sci. Jan. 26, 2004;6(1):E4.
Shire et al., Challenges in the development of high protein concentration formulations. J Pharm Sci. 2004;93:1390-402.
Sim et al., Branched polyethylene glycol for protein precipitation. Biotechnol Bioeng. Mar. 2012;109(3):736-46.
Sinha et al., Comparison of LC and LC/MS Methods for Quantifying N-Glycosylation in Recombinant IgGs. J Am Soc Mass Apectrum. 2008;19:1643-54.
Sinha et al., Poly-epsilon-caprolactone microspheres and nanospheres: an overview. Int J Pharm. Jun. 18, 2004;278(1):1-23.
Stock et al., Platelet-derived growth factor receptor-a: a novel therapeutic target in human hepatocellular cancer. Mol Cancer Ther. 2007;6:1932-41.
Sutyagin et al., Chemistry and Physics of Polymers: schoolbook. A.V. Publishing House TPU. 2003, p. 208.
Thurston et al., The complex role of angiopoietin-2 in the angiopoietin-tie signaling pathway. Cold Spring Harb Perspect Med. Sep. 1, 2012;2(9):a006550.
Towns, Moisture content in proteins: its effects and measurement. Chromatography A. 1995;705:115-27. (Abstract Only).
Treuheit et al., Inverse relationship of protein concentration and aggregation. Pharm Res. Apr. 2002;19(4):511-6.
Vehring, Pharmaceutical engineering via spray drying. Pharm Res. 2007;25:999-1022.
Vroman et al., Biodegradable Polymers. Materials 2009;2:307-44.
Wirtz et al., Transport properties of template synthesized gold and carbon nanotube membranes. Int J Nanosci. 2002;1(3,4):255.
Wu et al., A systems biology perspective on sVEGFR1: its biological function, pathogenic role and therapeutic use. J Cell Mol Med. Mar. 2010;14(3):528-52.
Wyati, Light scattering and the absolute characterization of macromolecules. Anal Chim Acta. 1993;272:1-40.
Yadav et al., Tumour Angiogenesis and Angiogenic Inhibitors: A Review. J Clin Diagn Res. Jun. 2015;9(6):XE01-XE05.
Yang et al., Reservoir-based polymer drug delivery systems. J Lab Autom. Feb. 2012;17(1):50-8.
Ye et al., Issues in long-term protein delivery using biodegradable microparticles. J Control Release. Sep. 1, 2010;146(2):241-60.
Yeo et al., A new microencapsulation method using an ultrasonic atomizer based on interfacial solvent exchange. J Control Release. Dec. 10, 2004;100(3):379-88.
Zachary, VEGF signalling: integration and multi-tasking in endothelial cell biology. Biochem Soc Trans. Dec. 2003;31(Pt 6):1171-7.
Brazilian Search Report and Written Opinion for Application No. 112018010743, dated Aug. 10, 2020, 6 pages.
Canadian Office Action dated Mar. 22, 2019, 5 pages.
Canadian Office Action for Application No. 3076725, dated Apr. 9, 2021, 4 pages.
Chilean Office Action for Application No. 2018001623, dated Aug. 18, 2020, 34 pages.
Chilean Office Action for corresponding Chilean application, dated Feb. 7, 2020, 3 pages.
Chinese Notification to Grant for Application No. 201280056324, dated Nov. 5, 2015, 3 pages.

(56) References Cited

OTHER PUBLICATIONS

Chinese Office Action for Application No. 201280056324, dated Jun. 2, 2015, 5 pages.
Chinese Office Action for Application No. 201610035281, dated Apr. 4, 2019, 11 pages.
Chinese Office Action for Application No. 201610035281, dated Jul. 4, 2018, 13 pages.
Chinese Office Action for Application No. 201680067420, dated Jun. 28, 2020, 20 pages.
Chinese Office Action for Application No. 201680067420, dated Nov. 18, 2020, 13 pages.
Chinese Office Action for Application No. 201680072951, dated Jun. 22, 2020, 18 pages.
Chinese Office Action for Application No. 201680072951, dated Mar. 26, 2021, 7 pages.
Chinese Office Action for Application No. 201680072951, dated Sep. 11, 2020, 8 pages.
Chinese Search Report for Application No. 201280056324, dated May 25, 2015, 2 pages.
Chinese Search Report for Application No. 201610035281, dated Jun. 26, 2018, 2 pages.
Chinese Search Report for Application No. 201680067420, dated Jun. 19, 2020, 1 page.
Chinese Search Report for Application No. 201680072951, dated Jun. 16, 2020, 2 pages.
Colombian Office Action for Application No. NC20180005920, dated May 2, 2020, 5 pages.
European Decision to Grant for Application No. 12795967, dated Jan. 8, 2020, 2 pages.
European Decision to Grant for Application No. 18173299, dated May 4, 2020, 2 pages.
European Notice of Allowance for Application No. 19180351, dated Mar. 5, 2021, 6 pages.
European Notice of Opposition for Application No. 12795967, dated Oct. 21, 2020, 19 pages.
European Office Action dated Jan. 10, 2018, 4 pages.
European Office Action dated Nov. 28, 2018.
European Office Action for Application No. 12795967, dated Apr. 12, 2019, 3 pages.
European Office Action for Application No. 12795967, dated Aug. 1, 2018, 4 pages.
European Office Action for Application No. 12795967, dated Jan. 10, 2018, 4 pages.
European Office Action for Application No. 12795967, dated Nov. 28, 2018, 4 pages.
European Office Action for Application No. 12795967, dated Nov. 3, 2020, 1 page.
European Office Action for Application No. 12795967, dated Sep. 23, 2019, 6 pages.
European Office Action for Application No. 16788338, dated Sep. 29, 2020, 5 pages.
European Office Action for Application No. 16799339.8, dated Sep. 30, 2020, 5 pages.
European Office Action for Application No. 16820541, dated Feb. 4, 2021, 4 pages.
European Office Action for Application No. 16820541, dated Jun. 16, 2020, 6 pages.
European Office Action for Application No. 16820541, dated Nov. 6, 2019, 6 pages.
European Office Action for Application No. 18173299, dated Feb. 27, 2020, 6 pages.
European Office Action for Application No. 18173299, dated Jul. 11, 2019, 5 pages.
European Office Action for Application No. 19180351, dated Sep. 25, 2020, 6 pages.
European Search Report and Search Opinion for Application No. 18173299, dated Aug. 8, 2018, 8 pages.
European Search Report and Search Opinion for Application No. 19180351, dated Aug. 21, 2019, 8 pages.
Indian Office Action for Application No. 201817015063, dated Jul. 8, 2020, 7 pages.
International Preliminary Report on Patentability for Application No. PCT/US2012/065735, dated May 30, 2014, 9 pages.
International Preliminary Report on Patentability for Application No. PCT/US2016/057019, dated Apr. 26, 2018, 8 pages.
International Preliminary Report on Patentability for Application No. PCT/US2016/067280, dated Jun. 28, 2018, 9 pages.
International Search Report and Written Opinion dated Jun. 18, 2018, 10 pages.
International Search Report and Written Opinion for Application No. PCT/US2012/065735, dated Feb. 15, 2013, 11 pages.
International Search Report and Written Opinion for Application No. PCT/US2016/067280, dated Mar. 10, 2017.
Israeli Office Action for the corresponding Israel application, dated Jun. 28, 2020, 4 pages.
Japanese Decision to Grant for Application No. 2014-542536, dated Dec. 4, 2017, 5 pages.
Japanese Decision to Grant for Application No. 2017-149732, dated Jun. 13, 2019, 6 pages.
Japanese Decision to Grant for Application No. 2019-079952, dated Jun. 3, 2020, 6 pages.
Japanese Office Action dated May 9, 2018, 11 pages.
Japanese Office Action for Application No. 2014-542536, dated Aug. 29, 2016, 12 pages.
Japanese Office Action for Application No. 2014-542536, dated Mar. 28, 2017, 12 pages.
Japanese Office Action for Application No. 2014-542536, dated Nov. 14, 2017, 6 pages.
Japanese Office Action for Application No. 2017-149732, Apr. 20, 2018, 22 pages.
Japanese Office Action for Application No. 2017-149732, dated Dec. 26, 2018, 24 pages.
Japanese Office Action for Application No. 2018-519460 dated Jun. 22, 2020, 2 pages.
Japanese Office Action for Application No. 2018-531166, dated Oct. 12, 2020, 13 pages.
Japanese Search Report for Application No. 2018-519460, dated Apr. 20, 2020, 48 pages.
Korean Grant of Patent for Application 10-2014-7014549, dated May 28, 2020, 2 pages.
Korean Office Action for Application No. 10-2014-7014549, dated Dec. 19, 2019, 6 pages.
Korean Office Action for Application No. 10-2014-7014549, dated Jun. 12, 2019, 11 pages.
Korean Office Action for Application No. 10-2020-7003704, dated May 6, 2020, 6 pages.
Korean Office Action for Application No. 10-2020-7003704, dated Nov. 20, 2020, 4 pages.
Korean Office Action for the corresponding Korean application, dated Dec. 19, 2019, 4 pages.
Mexican Office Action dated Nov. 1, 2017, 12 pages.
Mexican Office Action for Application No. 2018004695, dated Mar. 2, 2021, 7 pages.
Non-Final Office Action received for U.S. Appl. No. 15/766,586, dated Mar. 9, 2021, 19 pages.
Notice of Grounds for Rejection issued by the Korean Patent Office dated May 6, 2020 for the corresponding Korean application, 4 pages.
Report of opposition to European Patent No. 2790681, dated Nov. 10, 2020, 5 pages.
Russian Decision to Grant for Application No. 2014124682, dated Nov. 17, 2017, 13 pages.
Russian Office Action for Application No. 2018101248, dated Mar. 2, 2021, 16 pages.
Russian Search Report for Application No. 2018101248, dated Mar. 2, 2021, 4 pages.
Singapore Written Opinion dated Sep. 11, 2019, 9 pages.
Singapore Written Opinion for Application No. 11201402152Y, dated Nov. 13, 2017, 7 pages.
Singapore Written Opinion for Application No. 11201802867U, dated Jul. 17, 2020, 6 pages.

(56) References Cited

OTHER PUBLICATIONS

Singapore Written Opinion for Application No. 11201802867U, dated Mar. 28, 2019, 6 pages.
U.S. Advisory Action (PTOL-303) for U.S. Appl. No. 13/680,069, dated Mar. 9, 2016.
U.S. Final Office Action for U.S. Appl. No. 15/766,586, dated Nov. 18, 2020, 23 pages.
U.S. Final Office Action for U.S. Appl. No. 15/775,479, dated Nov. 16, 2020, 20 pages.
U.S. Final Rejection for U.S. Appl. No. 13/680,069, dated Jun. 20, 2014.
U.S. Final Rejection for U.S. Appl. No. 13/680,069, dated Nov. 6, 2015.
U.S. Non-Final Office Action for U.S. Appl. No. 15/766,586, dated Mar. 9, 2020, 19 pages.
U.S. Non-Final Office Action for U.S. Appl. No. 15/766,586, dated May 21, 2020, 19 pages.
U.S. Non-Final Rejection for U.S. Appl. No. 13/680,069, dated Dec. 17, 2013.
U.S. Non-Final Rejection for U.S. Appl. No. 13/680,069, dated Dec. 5, 2016.
U.S. Non-Final Rejection for U.S. Appl. No. 13/680,069, dated Mar. 31, 2015.
U.S. Non-Final Rejection for U.S. Appl. No. 15/775,479, dated May 11, 2020.
US Patent Assignment No. 61561525.
U.S. Requirement for Restriction/Election for U.S. Appl. No. 13/680,069, dated Aug. 21, 2013.
U.S. Requirement for Restriction/Election for U.S. Appl. No. 15/775,479, dated Mar. 5, 2020.

SEQUENCE LISTING

```
<160> NUMBER OF SEQ ID NOS: 1

<210> SEQ ID NO 1
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Ile Ile His Met Thr Glu Gly Arg Glu Leu Val Ile Pro Cys Arg Val
1               5                   10                  15

Thr Ser Pro Asn Ile Thr Val Thr Leu Lys Lys Phe Pro Leu Asp Thr
            20                  25                  30

Leu Ile Pro Asp Gly Lys Arg Ile Ile Trp Asp Ser Arg Lys Gly Phe
        35                  40                  45

Ile Ile Ser Asn Ala Thr Tyr Lys Glu Ile Gly Leu Leu Thr Cys Glu
50                  55                  60

Ala Thr Val Asn Gly His Leu Tyr Lys Thr Asn Tyr Leu Thr His Arg
65                  70                  75                  80

Gln Thr Asn Thr Ile Ile Asp Val Val Leu Ser Pro Ser His Gly Ile
                85                  90                  95

Glu Leu Ser Val Gly Glu Lys Leu Val Leu Asn Cys Thr Ala Arg Thr
            100                 105                 110

Glu Leu Asn Val Gly Ile Asp Phe Asn Trp Glu Tyr Pro Ser Ser Lys
            115                 120                 125

His Gln His Lys Lys Leu Val Asn Arg Asp Leu Lys Thr Gln Ser Gly
        130                 135                 140

Ser Glu Met Lys Lys Phe Leu Ser Thr Leu Thr Ile Asp Gly Val Thr
145                 150                 155                 160

Arg Ser Asp Gln Gly Leu Tyr Thr Cys Ala Ala Ser Ser Gly Leu Met
                165                 170                 175

Thr Lys Lys Asn Ser Thr Phe Val Arg Val His Glu Lys Asp Lys Thr
            180                 185                 190

His Thr Cys Pro Pro Cys Pro Ala Pro Glu Leu Leu Gly Gly Pro Ser
        195                 200                 205

Val Phe Leu Phe Pro Pro Lys Pro Lys Asp Thr Leu Met Ile Ser Arg
210                 215                 220

Thr Pro Glu Val Thr Cys Val Val Val Asp Val Ser His Glu Asp Pro
225                 230                 235                 240

Glu Val Lys Phe Asn Trp Tyr Val Asp Gly Val Glu Val His Asn Ala
            245                 250                 255

Lys Thr Lys Pro Arg Glu Glu Gln Tyr Asn Ser Thr Tyr Arg Val Val
        260                 265                 270

Ser Val Leu Thr Val Leu His Gln Asp Trp Leu Asn Gly Lys Glu Tyr
        275                 280                 285

Lys Cys Lys Val Ser Asn Lys Ala Leu Pro Ala Pro Ile Glu Lys Thr
290                 295                 300

Ile Ser Lys Ala Lys Gly Gln Pro Arg Glu Pro Gln Val Tyr Thr Leu
305                 310                 315                 320

Pro Pro Ser Arg Asp Glu Leu Thr Lys Asn Gln Val Ser Leu Thr Cys
            325                 330                 335

Leu Val Lys Gly Phe Tyr Pro Ser Asp Ile Ala Val Glu Trp Glu Ser
            340                 345                 350

Asn Gly Gln Pro Glu Asn Asn Tyr Lys Thr Thr Pro Pro Val Leu Asp
        355                 360                 365

Ser Asp Gly Ser Phe Phe Leu Tyr Ser Lys Leu Thr Val Asp Lys Ser
        370                 375                 380

Arg Trp Gln Gln Gly Asn Val Phe Ser Cys Ser Val Met His Glu Ala
385                 390                 395                 400

Leu His Asn His Tyr Thr Gln Lys Ser Leu Ser Leu Ser Pro Gly
            405                 410                 415
```

POLYMER PROTEIN MICROPARTICLES

CROSS-REFERENCE TO RELATED APPLICATIONS

This application is a continuation application of U.S. patent application Ser. No. 15/450,335, filed on Mar. 6, 2017, which is a divisional of U.S. patent application Ser. No. 13/680,069, filed Nov. 18, 2012, which claims priority to U.S. Provisional Patent Application No. 61/561,525, filed Nov. 18, 2011, all of which are herein specifically incorporated by reference in their entirety.

SEQUENCE LISTING

The instant application contains a Sequence Listing which has been submitted electronically in ASCII format and is hereby incorporated by reference in its entirety. Said ASCII copy, created on Apr. 4, 2022, is named 135975-11104_SL.txt and is 4,031 bytes in size.

FIELD

The invention relates to the manufacture, composition, and use of an extended release protein therapeutic. Specifically, the invention relates to the manufacture, composition, and use of a plurality of polymer coated protein microspheres for the extended and uniform release of protein in an aqueous-based or physiological environment over time.

BACKGROUND

The extended release of a therapeutic protein administered toward a biological target, such as e.g., the retina or a tumor, or administered parenterally is desirable for the treatment of many different conditions, including cancers, cardiovascular diseases, vascular conditions, orthopedic disorders, dental disorders, wounds, autoimmune diseases, gastrointestinal disorders, and ocular diseases. Biocompatible and biodegradable polymers for the controlled and extended delivery of drugs have been in use for decades. As the polymer degrades over time, the therapeutic drug is slowly released.

In the case of intraocular therapeutics, there is a significant unmet medical need for extended release formulations to deliver protein therapeutics effectively over time with as few intraocular injections as possible. In the case of other diseases, such as cancer, diseases of inflammation, and other diseases, there is a need for improved implantable extended release formulations containing protein therapeutics.

Applicants have discovered and herein disclose and claim methods of manufacturing and using microparticles containing a biodegradable polymer and a therapeutic protein, which is capable of releasing a therapeutically effective amount of the therapeutic protein uniformly over an extended period of time.

SUMMARY

In one aspect, the invention provides a microparticle comprising a protein coated with a polymer. In one embodiment, the microparticle has a diameter of from about 2 microns to about 70 microns. In one embodiment, the microparticle has a diameter of about 15 microns.

In one embodiment, the protein is an antigen-binding protein. In one embodiment, the protein comprises an Fc domain. In one embodiment, the protein comprises a receptor domain. In one embodiment, the protein is an antibody. In another embodiment, the protein is a receptor-Fc-fusion protein. In another embodiment, the protein is a trap-type protein, which comprises a cognate-receptor fragment and an Fc domain. In one particular embodiment, the protein is a VEGF-Trap protein. In one embodiment, the VEGF-Trap protein comprises an amino acid sequence set forth in SEQ ID NO:1.

In one embodiment, the polymer is a biodegradable polymer. In some embodiments, the polymer is selected from the group consisting of polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyanoacrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polyleucine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly (butylene terephthalate) copolymer, and combinations and copolymers thereof. In one embodiment, the polymer is poly-ε-caprolactone (PCL) or a derivative or copolymer thereof. In one embodiment, the polymer is PLGA or a derivative or copolymer thereof. In one embodiment, the polymer is ethyl cellulose or a derivative or copolymer thereof. In one embodiment, the polymer is polyorthoester or a derivative or copolymer thereof.

In one embodiment, the microparticle comprises a micronized protein core of less that ten microns and a polymer cortex. In one embodiment, the micronized protein core is at least 50% coated with polymer, which means that no more than 50% of the surface of the micronized protein core is exposed. In one embodiment, at least 60%, at least 70%, at least 80%, at least 90%, at least 95%, at least 99%, or 100% of the surface of the micronized protein core is coated with polymer.

In one embodiment, the microparticle of greater than 10 microns in size comprises (a) a micronized protein core of less that 10 microns, wherein the protein is any one or more of an antibody or antibody fragment, a receptor or soluble fragment thereof, a soluble T-cell receptor fragment, a soluble MHC fragment, a receptor-Fc-fusion protein, a trap-type protein, and a VEGF-Trap protein; and (b) a polymer coat, wherein the polymer is any one or more of a biocompatible polymer, a biodegradable polymer, a bioerodible polymer, polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-8-R-hydroxy butyrate (PHB), poly-8-R-hydroxy alkanoate (PHA), poly-8-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylysine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof.

In one embodiment, the microparticle of an average diameter of about 15 microns to about 30 microns comprises (a) a micronized protein core of about 10 to about 12 microns, wherein the protein is a VEGF-Trap protein; and (b) a polymer coat, wherein the polymer is any one or more of PCL, PLGA, ethyl cellulose and polyorthoester, and copolymers or derivatives thereof.

In one aspect, the invention provides a plurality of microparticles, which range in size from about two microns to about 70 microns, and which comprise a micronized protein core of about two microns to about 30 microns, and a polymer cortex.

In one embodiment, the protein is an antigen-binding protein. In some embodiments, the antigen-binding protein is any one or more of an antibody or antibody fragment, a receptor or soluble fragment thereof, a soluble T-cell receptor fragment, a soluble MHC fragment, a receptor-Fc-fusion protein, a trap-type protein, and a VEGF-Trap protein. In one embodiment, the protein comprises an Fc domain. In one embodiment, the protein is an antibody. In another embodiment, the protein is a receptor-Fc-fusion protein. In another embodiment, the protein is a trap-type protein, which comprises a cognate-receptor fragment and an Fc domain. In one particular embodiment, the protein is a VEGF-Trap protein. In a specific embodiment, the VEGF-Trap protein comprises the amino acid sequence set forth in SEQ ID NO:1.

In one embodiment, the polymer is a biocompatible polymer. In one embodiment, the polymer is a bioerodible polymer. In one embodiment, the polymer is a biodegradable polymer. In some embodiments, the polymer is selected from the group consisting of polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidyleholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polyleucine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof. In one embodiment, the polymer is poly-ε-caprolactone (PCL) or a derivative or copolymer thereof. In one embodiment, the polymer is PLGA or a derivative or copolymer thereof. In one embodiment, the polymer is ethyl cellulose or a derivative or copolymer thereof. In one embodiment, the polymer is a polyorthoester incorporating a latent acid.

In one embodiment, the micronized protein core of most microparticles of the plurality of microparticles is at least 50% coated with polymer, which means that no more than 50% of the surface of the micronized protein core is exposed. In one embodiment, at least 60%, at least 70%, at least 80%, at least 90%, at least 95%, at least 99%, or 100% of the surface of the micronized protein core is coated with polymer.

In one embodiment, the plurality of microparticles, which range in size from about two microns to about 70 microns, comprise (a) a micronized protein core of from about two microns to about 30 microns, wherein the protein is any one or more of an antibody or antibody fragment, a receptor or soluble fragment thereof, a soluble T-cell receptor fragment, a soluble MHC fragment, a receptor-Fc-fusion protein, a trap-type protein, and a VEGF-Trap protein; and (b) a polymer cortex, wherein the polymer is any one or more of a biocompatible polymer, a biodegradable polymer, a bioerodible polymer, polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), poly-ε-caprolactone (PCL), poly-alkyl-cyano-acrylate (polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA)), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylysine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof.

In one embodiment, the plurality of microparticles, which range in size from about two microns to about 70 microns, with a median size of from about 15 microns to about 30 microns, comprise (a) a micronized protein core of from about two microns to about 30 microns, with a median size of about 10 microns to about 12 microns, wherein the protein is a VEGF-Trap protein; and (b) a polymer cortex, wherein the polymer is any one or more of PLA, PCL, PLGA, ethyl cellulose and polyorthoester, and copolymers or derivatives thereof.

In one aspect, the invention provides a method of manufacturing a microparticle, which comprises a protein core and a polymer cortex. In one embodiment, the manufactured microparticle has a diameter of about two microns to about 70 microns, or a median diameter of about 15 microns to about 30 microns. In one embodiment, the method of manufacturing the microparticle comprises (1) obtaining a protein particle; (2) suspending the protein particle in a solution comprising the polymer and a solvent; and (3) removing the solvent, wherein a microparticle is formed comprising the protein core coated with the polymer cortex.

In one embodiment, the protein particle of step (1) is a micronized protein particle, which is obtained by spray drying a solution comprising the protein. In some embodiments, the protein solution is spray dried via dual-nozzle sonication, single-nozzle sonication, or electrospray. In some embodiments, the resultant micronized protein particle, which forms the core of the manufactured microparticle, has a diameter of from about two microns to about 30 microns, with a median diameter of about 10 microns to about 12 microns.

In some embodiments, the protein which forms the core is an antigen-binding protein. In some embodiments, the antigen-binding protein is any one or more of an antibody (e.g., IgG) or antibody fragment, a receptor or soluble fragment thereof, a soluble T-cell receptor fragment, a soluble MHC fragment, a receptor-Fc-fusion protein, a trap-type protein, and a VEGF-Trap protein. In a specific embodiment, the protein is a VEGF-Trap comprising the amino acid sequence set forth in SEQ ID NO:1.

In one embodiment, the solvent is removed at step (3) by creating a dispersion of the protein-polymer-solvent mixture of step (2) and allowing the solvent to evaporate from the droplets created by the dispersion. In one embodiment, the dispersion is created by spray-drying, which may be performed by dual-nozzle sonication, single-nozzle sonication, or electrospray. In one embodiment, the solvent is removed from the droplets by applying heat or air, or by chemical extraction.

In one embodiment, the polymer is biodegradable, bioerodible, and/or biocompatible. In some embodiments, the polymer is any one or more of polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylysine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof. In one embodiment, the polymer is poly-ε-caprolactone (PCL) or a derivative or copolymer thereof. In one embodiment, the polymer is PLGA or a derivative or copolymer thereof. In one embodiment, the polymer is ethyl cellulose or a derivative or copolymer thereof. In one embodiment, the polymer is polyorthoester, or a derivative thereof, which contains acid labile elements. In another embodiment, the polymer is PLA.

In one aspect, the invention provides a method of manufacturing a microparticle comprising the steps of (1) forming a micronized protein particle having a diameter of from about two microns to about 30 microns, with a median diameter of from about 10 microns to 12 microns, by spray-drying a solution containing a protein, wherein the protein is an antigen-binding protein. In some embodiments, the antigen-binding protein is any one or more of an antibody or antibody fragment, a receptor or soluble fragment thereof, a soluble T-cell receptor fragment, a soluble MHC fragment, a receptor-Fc-fusion protein, a trap-type protein, and a VEGF-Trap protein (e.g., one having the sequence of SEQ ID NO:1); (2) suspending the micronized protein particle in a solution comprising the polymer and a solvent, wherein the polymer is any one or more of a biodegradable polymer, a bioerodible polymer, a biocompatible polymer, polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polyleucine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof; and (3) removing the solvent by spray-drying micronized protein particle-polymer-solvent suspension and driving off the solvent by applying heat or air, or by extracting the solvent, wherein a microparticle is formed having a diameter of about two microns to about 70 microns, with a median diameter of from about 15 microns to about 30 microns, and comprising a protein core and a polymer cortex.

In some embodiments, the spray-drying of step (1) or step (3) is performed via dual-nozzle sonication, single-nozzle sonication, or electrospray.

In one embodiment, the method of manufacturing the microparticle comprises the steps of (1) forming a micronized VEGF-Trap particle having a diameter of from about 10 microns to 12 microns by spray-drying a solution containing a VEGF Trap protein; (2) suspending the micronized VEGF Trap particle in a solution comprising polyorthoester incorporating a latent acid and a compatible solvent, or ethylcellulose and a compatible solvent; and (3) removing the solvent by (a) spray-drying the micronized VEGF Trap particle-polyorthoester-latent acid-solvent suspension or the micronized VEGF Trap particle-ethyl cellulose-solvent suspension and (b) driving off the solvent by applying heat or air, or by extracting the solvent, wherein a microparticle is formed having a diameter of about 15 microns to about 30 microns, and comprising a VEGF-Trap core and a polymer cortex of polyorthoester, and copolymers or derivatives thereof.

In one aspect, the invention provides an extended release formulation of a therapeutic protein for the release or delivery of a steady level of the therapeutic protein over time. The extended release formulation comprises a plurality of microparticles, which range in size from about two microns to about 70 microns, each of which comprises a micronized protein core of about two microns to about 30 microns, and a polymer cortex.

In one embodiment, the therapeutic protein is an antigen-binding protein. In some embodiments, the antigen-binding protein is any one or more of an antibody (e.g., IgG) or antibody fragment, a receptor or soluble fragment thereof, a soluble T-cell receptor fragment, a soluble MHC fragment, a receptor-Fc-fusion protein, a trap-type protein, and a VEGF-Trap protein (e.g., one of which has a primary structure of SEQ ID NO:1). In one embodiment, the therapeutic protein comprises an Fc domain. In one embodiment, the protein is an antibody. In another embodiment, the protein is an IgG. In another embodiment, the therapeutic protein is a receptor-Fc-fusion protein. In another embodiment, the therapeutic protein is a trap-type protein, which comprises a cognate-receptor fragment and an Fc domain. In one particular embodiment, the therapeutic protein is a VEGF-Trap protein. In yet another embodiment, the VEGF-Trap comprises the amino acid sequence set forth in SEQ ID NO:1.

In one embodiment, the polymer cortex comprises a biocompatible polymer. In one embodiment, the polymer cortex comprises a bioerodible polymer. In one embodiment, the polymer cortex comprises a biodegradable polymer. In some embodiments, the polymer cortex comprises a polymer selected from the group consisting of polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy) hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycoldistearoylphosphatidylehtanolamine (DOPC/PEG-DS-PE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polyleucine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly (butylene terephthalate) copolymer, and combinations and copolymers thereof. In one embodiment, the polymer is poly-ε-caprolactone (PCL) or a derivative or copolymer thereof. In one embodiment, the polymer cortex comprises a PLGA. In one embodiment, the polymer cortex comprises an ethyl cellulose. In one embodiment, the polymer cortex comprises any one or more of PLA, PLGA, ethyl cellulose, and polyorthoester, and copolymers or derivatives thereof.

In one embodiment, plurality of microparticles comprises a collection of microparticles having a range of thicknesses of the polymer cortex, such that individual microparticles of the collection of microparticles degrades at a different rate, which allows for a uniform rate of release of the therapeutic protein.

In one embodiment, the plurality of microparticles comprises a mixture of uncoated micronized protein particles and microparticles having a range of thicknesses of the polymer cortex, which allows for the release of therapeutic protein at periodic intervals based on cortex thickness.

In one embodiment, the plurality of microparticles comprises a mixture of microparticles having polymer cortices of varying levels of hydrophobicity to control the timing or duration of degradation and subsequent release. In one embodiment, the microparticles each comprise an inner polymer layer and an outer polymer layer, wherein the outer polymer layer limits the hydration of the inner polymer layer to control release of the therapeutic protein.

In one embodiment, the therapeutic protein is released from the plurality of microparticles at a rate of from about 0.01 mg/week to about 0.30 mg/week for a duration of at least 60 days, when the microparticles are in an aqueous environment. In one embodiment, the aqueous environment is in vitro buffer. In one embodiment, the aqueous environment is in vivo. In one embodiment, the aqueous environment is ex vivo. In one embodiment, the aqueous environment is a vitreous humor.

In one embodiment, the extended release formulation comprises a plurality of microparticles, which range in size from about two microns to about 70 microns and which comprise (a) a core of micronized therapeutic protein of from about two microns to about 30 microns, wherein the therapeutic protein is an antigen-binding protein, which in some cases can be any one or more of an antibody or antibody fragment, a receptor or soluble fragment thereof, a soluble T-cell receptor fragment, a soluble MHC fragment, a receptor-Fc-fusion protein, a trap-type protein, and a VEGF-Trap protein; and (b) a polymer cortex of a range of thicknesses, wherein the polymer is any one or more of a biocompatible polymer, a biodegradable polymer, a bioerodible polymer, polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly(ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, polysaccharides, cellulose, ethyl cellulose, methyl cellulose, alginates, dextran and dextran hydrogel polymers, amylose, inulin, pectin and guar gum, chitosan, chitin, heparin, hyaluronic acid, cyclodextrin (CD)-based polyrotaxanes and polypseudorotaxanes, polyaspartates, polyglutamates, polylysine, leucine-glutamate co-polymers, polybutylene succinate (PBS), gelatin, collagens, fibrins, fibroin, polyorthoesters, polyorthoester-polyamidine copolymer, polyorthoester-diamine copolymers, polyorthoesters incorporating latent acids, poly(ethylene glycol)/poly(butylene terephthalate) copolymer, and combinations and copolymers thereof, wherein the microparticles release or deliver a steady level of the therapeutic protein at a rate of from about 0.01 mg/week to about 0.30 mg/week for at least 60 days.

In one embodiment, the extended release formulation comprises a plurality of microparticles, which range in size from about two microns to about 70 microns, with a median size of from about 15 microns to about 30 microns, and which comprise (a) a micronized protein core of from about two microns to about 30 microns, with a median size of about 10 microns to about 12 microns, wherein the protein is a VEGF-Trap protein; and (b) a polymer cortex of a range of thicknesses, wherein the polymer is any one or more of PLGA, ethyl cellulose, and polyorthoester, and copolymers or derivatives thereof, such that in an aqueous environment the microparticles release or deliver a steady level of VEGF Trap at a rate of about 0.06±0.02 mg/week for at least 60 days.

In one aspect, the invention provides a method for modulating the release of a protein. In one embodiment, the method comprises the step of making a plurality of microparticles as described in the previous aspect, followed by the step of placing the microparticles into a solvent. The solvent in some embodiments is aqueous. The solvent can be in vitro, such as in a phosphate buffered solution. The solvent can be in vivo, such as e.g. vitreous humor.

DRAWINGS

FIG. 1 depicts the relative amount (% volume) of protein particles without a polymer cortex of a given diameter (ECD (μm)) in a population of protein particles manufactured from 50 mg/mL of VEGF Trap protein, 25 mg/mL of VEGF Trap protein, and 25 mg/mL of VEGF Trap protein plus 0.1% polysorbate 80.

Figure 2:
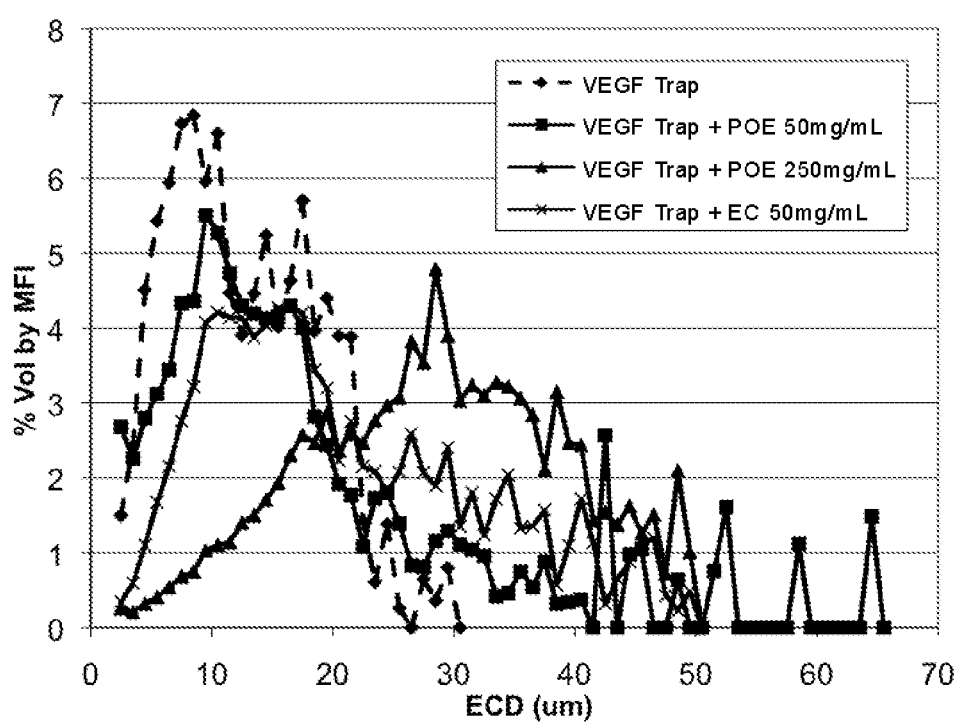

FIG. 2 depicts the relative amount (% volume determined by MFI) of microparticles of a given diameter (ECD (μm)) in a population of microparticles manufactured from 50 mg/mL of VEGF Trap protein plus 50 mg/mL POE, 250 mg/mL POE, and 50 mg/mL EC.

Figure 3:
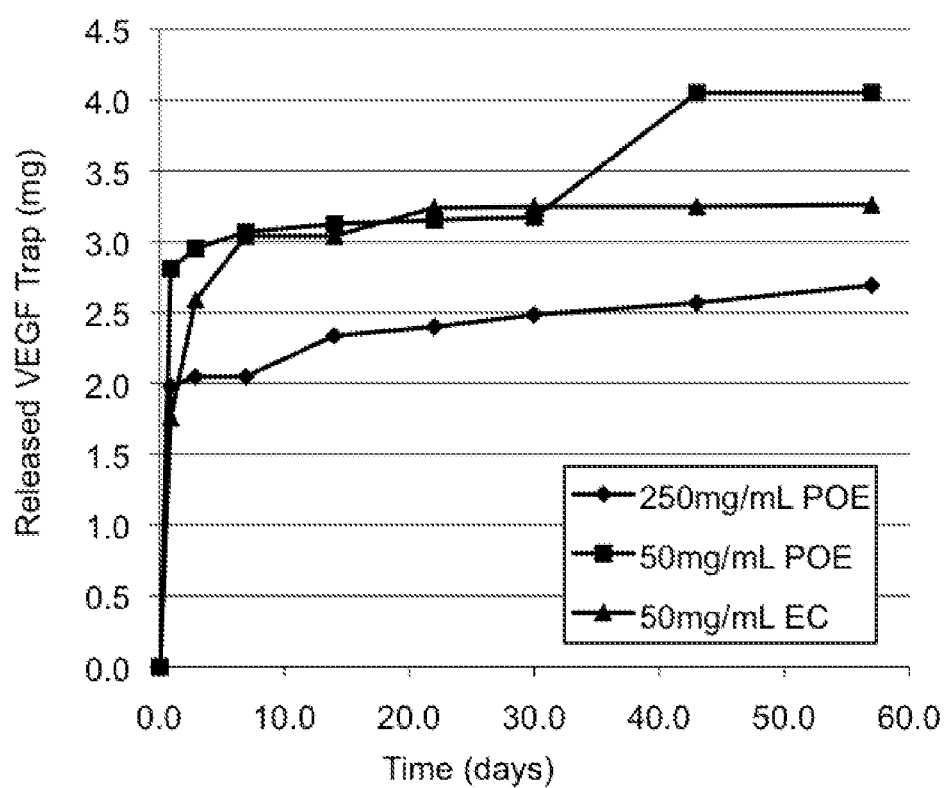

FIG. 3 depicts the amount of VEGF Trap protein in milligrams released from microparticles manufactured from 50 mg/mL POE, 250 mg/mL POE, or 50 mg/mL EC over approximately 60 days.

DETAILED DESCRIPTION

The micro particle and protein core particle of the subject invention are roughly spherical in shape. Some microparticles and protein cores will approach sphericity, while others will be more irregular in shape. Thus, as used herein, the term "diameter" means each and any of the following: (a) the diameter of a sphere which circumscribes the microparticle or protein core, (b) the diameter of the largest sphere that fits within the confines of the microparticle or the protein core, (c) any measure between the circumscribed sphere of (a) and the confined sphere of (b), including the mean between the two, (d) the length of the longest axis of the microparticle or protein core, (e) the length of the shortest axis of the microparticle or protein core, (f) any measure between the length of the long axis (d) and the length of the short axis (e), including the mean between the two, and/or (g) equivalent circular diameter ("ECD"), as determined by micro-flow imaging (MFI), nanoparticle tracking analysis (NTA), or light obscuration methods such as dynamic light scattering (DLS). See generally Sharma et al., Micro-flow imaging: flow microscopy applied to sub-visible particulate analysis in protein formulations, AAPS J. 2010 September; 12(3): 455-64. Diameter is generally expressed in micrometers (μm or micron). Diameter can be determined by optical measurement "Micronized protein particle" or "protein particle" means a particle containing multiple molecules of protein with low, very low, or close to zero amounts of water (e.g., <3% water by weight). As used herein, the micronized protein particle is generally spherical in shape and has an ECD ranging from 2 microns to about 35 microns. The micronized protein particle is not limited to any particular protein entity, and is suited to the preparation and delivery of a therapeutic protein. Common therapeutic proteins include inter alia antigen-binding proteins, such as e.g., soluble receptor fragments, antibodies (including IgGs) and derivatives or fragments of antibodies, other Fc containing proteins, including Fc fusion proteins, and receptor-Fc fusion proteins, including the trap-type proteins (Huang, C., Curr. Opin. Biotechnol. 20: 692-99 (2009)) such as e.g. VEGF-Trap.

The micronized protein particle of the invention can be made by any method known in the art for making micron-sized protein particles. For example, the protein particle may be made by inter alia spray-drying (infra), lyophilization, jet milling, hanging drop crystallization (Ruth et al., Acta Crystallographica D56: 524-28 (2000)), gradual precipitation (U.S. Pat. No. 7,998,477 (2011)), lyophilization of a protein-PEG (polyethylene glycol) aqueous mixture (Morita et al., Pharma. Res. 17: 1367-73 (2000)), supercritical fluid precipitation (U.S. Pat. No. 6,063,910 (2000)), or high pressure carbon dioxide induced particle formation (Bustami et al., Pharma. Res. 17: 1360-66 (2000)).

As used herein, the term "protein" refers to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies and chimeric or fusion proteins. Polypeptides are produced by recombinant animal cell lines using cell culture methods.

An "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

"Fc fusion proteins" comprise part or all of two or more proteins, one of which is an Fc portion of an immunoglobulin molecule, that are not fused in their natural state. Preparation of fusion proteins comprising certain heterologous polypeptides fused to various portions of antibody-derived polypeptides (including the Fc domain) has been described, e.g., by Ashkenazi et al., Proc. Natl. Acad. Sci. USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). For example, an Fc-fusion protein is a trap, such as for example an IL-1 trap (e.g., Rilonacept, which contains the IL-1RAcP ligand binding region fused to the IL-1R1 extracellular region fused to Fc of hIgG1; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flk1 fused to Fc of hIgG1; e.g., SEQ ID NO:1; see U.S. Pat. Nos. 7,087,411 and 7,279,159, which are herein incorporated by reference in their entirety).

As used herein, the term "polymer" refers to a macromolecule comprising repeating monomers connected by covalent chemical bonds. Polymers used in the practice of this invention are biocompatible and biodegradable. A biocompatible and biodegradable polymer can be natural or synthetic. Natural polymers include polynucleotides, polypeptides, such as naturally occurring proteins, recombinant proteins, gelatin, collagens, fibrins, fibroin, polyaspartates, polyglutamates, polylysine, leucine-glutamate co-polymers; and polysaccharides, such as cellulose alginates, dextran and dextran hydrogel polymers, amylose, inulin, pectin and guar gum, chitosan, chitin, heparin, and hyaluronic acid. Synthetic biocompatible or biodegradable polymers include polylactic acid (PLA), polyglycolic acid (PGA), polylactic-polyglycolic copolymer (PLGA), poly-D,L-lactide-co-glycolide (PLGA), PLGA-ethylene oxide fumarate, PLGA-alpha-tocopheryl succinate esterified to polyethylene glycol 1000 (PLGA-TGPS), polyanhydride poly[1,6-bis(p-carboxyphenoxy)hexane] (pCPH), poly(hydroxybutyric acid-cohydroxyvaleric acid) (PHB-PVA), polyethylene glycol-poly (lactic acid) copolymer (PEG-PLA), poly-ε-caprolactone (PCL), poly-alkyl-cyano-acrylate (PAC), poly (ethyl)cyanoacrylate (PEC), polyisobutyl cyanoacrylate, poly-N-(2-hydroxypropyl)methacrylamide (poly(HPMA)), poly-β-R-hydroxy butyrate (PHB), poly-β-R-hydroxy alkanoate (PHA), poly-β-R-malic acid, phospholipid-cholesterol polymers, 2-dioleoyl-sn-glycero-3-phosphatidylcholine/polyethyleneglycol-distearoylphosphatidylehtanolamine (DOPC/PEG-DSPE)/Cholesterol, ethyl cellulose, cyclodextrin (CD)-based polyrotaxanes and polypseudorotaxanes, polybutylene succinate (PBS), polyorthoesters, polyorthoester-polyamidine copolymers, polyorthoester-diamine copolymers, polyorthoesters incorporating latent acids torn control rates of degradation, and inter alia poly (ethylene glycol)/poly(butylene terephthalate) copolymers.

Ethyl cellulose (EC) is a well-known and readily available biomaterial used in the pharmaceutical and food sciences. It is a cellulose derivative in which some of the glucose hydroxyl groups are replaced with ethyl ether. See Martinac et al., J. Microencapsulation, 22(5): 549-561 (2005) and references therein, which describe methods of using ethyl cellulose as biocompatible polymers in the manufacture of microspheres. See also U.S. Pat. No. 4,210,529 (1980) and references therein for a detailed description of ethyl cellulose and methods of making derivatives of ethyl cellulose.

Poly-D,L-lactide-co-glycolide (PLGA) is also a well-known Food and Drug Administration (FDA) approved biocompatible and biodegradable polymer used in tissue engineering and pharmaceutical delivery systems. PLGA is a polyester comprising glycolic acid and lactic acid monomers. For a description of the synthesis of PLGA and manufacture of PLGA nanoparticles, see Astete and Sabliov, Biomater. Sci. Polym. Ed., 17(3): 247-89 (2006) and references therein.

Poly-ε-caprolactone (PCL) is another biocompatible and biodegradable polymer approved by the FDA for use in humans as a drug delivery device. PCL is a polyester of ε-caprolactone, which hydrolyses rapidly in the body to form a non-toxic or low toxicity hydroxycarboxylic acid. For a description of the manufacture of PCL, see Labet and Thielemans, Chemical Society Reviews 38: 3484-3504 (2009) and references therein. For a description of the manufacture and use of PCL-based microspheres and nanospheres as delivery systems, see Sinha et al., Int. J. Pharm., 278(1): 1-23 (2004) and references therein.

Polyorthoester (POE) is a bioerodible polymer designed for drug delivery. It is generally a polymer of a ketene acetal, preferably a cyclic diketene acetal, such as e.g., 3,9-dimethylene-2,4,8,10-tetraoxa spiro[5.5]-undecane, which is polymerized via glycol condensation to form the orthoester linkages. A description of polyorthoester synthesis and various types can be found e.g. in U.S. Pat. No. 4,304,767. Polyorthoesters can be modified to control their drug release profile and degradation rates by swapping in or out various hydrophobic diols and polyols, such as e.g., replacing a hexanetriol with a decanetriol; as well as adding latent acids, such as e.g., octanedioic acid or the like, to the backbone to increase pH sensitivity. Other modifications to the polyorthoester include the integration of an amine to increase functionality. The formation, description, and use of polyorthoesters are described in U.S. Pat. Nos. 5,968,543; 4,764,364; Heller and Barr, Biomacromolecules, 5(5): 1625-32 (2004); and Heller, Adv. Drug. Deliv. Rev., 57: 2053-62 (2005).

As used herein, the phrase "spray-dry" means a method of producing a dry powder comprising micron-sized particles from a slurry or suspension by using a spray-dryer. Spray dryers employ an atomizer or spray nozzle to disperse the suspension or slurry into a controlled drop size spray. Drop sizes from 10 to 500 µm can be generated by spray-drying. As the solvent (water or organic solvent) dries, the protein substance dries into a micron-sized particle, forming a powder-like substance; or in the case of a protein-polymer suspension, during drying, the polymer hardened shell around the protein load.

The microparticles of the invention comprise a protein core surrounded by a polymer cortex or coat. Briefly, a micronized protein particle is formed, which is then dispersed in a polymer solution (polymer dissolved in solvent) to form a protein-polymer suspension. The protein-polymer suspension is then dispersed into micronized (atomized) droplets, and the solvent is driven-off to form the microparticle.

In one embodiment, the micronized protein particle is formed by making a solution of the protein and then subjecting that protein solution to dispersion and heat to form a dry powder comprising the protein. One method to form the micronized protein particles is by spray-drying. In one embodiment, the protein is a therapeutic protein that is formulated to include buffers, stabilizers and other pharmaceutically acceptable excipients to make a pharmaceutical formulation of the therapeutic protein. Exemplary pharmaceutical formulations are described in U.S. Pat. Nos. 7,365,165, 7,572,893, 7,608,261, 7,655,758, 7,807,164, US 2010-0279933, US 2011-0171241, and PCT/US11/54856.

The amount of therapeutic protein contained within the pharmaceutical formulations of the present invention may vary depending on the specific properties desired of the formulations, as well as the particular circumstances and purposes for which the formulations are intended to be used. In certain embodiments, the pharmaceutical formulations may contain about 1 mg/mL to about 500 mg/mL of protein; about 5 mg/mL to about 400 mg/mL of protein; about 5 mg/mL to about 200 mg/mL of protein; about 25 mg/mL to about 180 mg/mL of protein; about 25 mg/mL to about 150 mg/mL of protein; or about 50 mg/mL to about 180 mg/mL of protein. For example, the formulations of the present invention may comprise about 1 mg/mL; about 2 mg/mL; about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 86 mg/mL; about 87 mg/mL; about 88 mg/mL; about 89 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 131 mg/mL; about 132 mg/mL; about 133 mg/mL; about 134 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; about 200 mg/mL; about 205 mg/mL; about 210 mg/mL; about 215 mg/mL; about 220 mg/mL; about 225 mg/mL; about 230 mg/mL; about 235 mg/mL; about 240 mg/mL; about 245 mg/mL; about 250 mg/mL; about 255 mg/mL; about 260 mg/mL; about 265 mg/mL; about 270 mg/mL; about 275 mg/mL; about 280 mg/mL; about 285 mg/mL; about 200 mg/mL; about 200 mg/mL; or about 300 mg/mL of therapeutic protein.

The pharmaceutical formulations of the present invention comprise one or more excipients. The term "excipient," as used herein, means any non-therapeutic agent added to the formulation to provide a desired consistency, viscosity or stabilizing effect.

The pharmaceutical formulations of the present invention may also comprise one or more carbohydrate, e.g., one or more sugar. The sugar can be a reducing sugar or a non-reducing sugar. "Reducing sugars" include, e.g., sugars with a ketone or aldehyde group and contain a reactive hemiacetal group, which allows the sugar to act as a reducing agent. Specific examples of reducing sugars include fructose, glucose, glyceraldehyde, lactose, arabinose, mannose, xylose, ribose, rhamnose, galactose and maltose. Non-reducing sugars can comprise an anomeric carbon that is an acetal and is not substantially reactive with amino acids or polypeptides to initiate a Maillard reaction. Specific examples of non-reducing sugars include sucrose, trehalose, sorbose, sucralose, melezitose and raffinose. Sugar acids include, for example, saccharic acids, gluconate and other polyhydroxy sugars and salts thereof.

The amount of sugar contained within the pharmaceutical formulations of the present invention will vary depending on the specific circumstances and intended purposes for which the formulations are used. In certain embodiments, the formulations may contain about 0.1% to about 20% sugar; about 0.5% to about 20% sugar; about 1% to about 20% sugar; about 2% to about 15% sugar; about 3% to about 10% sugar; about 4% to about 10% sugar; or about 5% to about 10% sugar. For example, the pharmaceutical formulations of the present invention may comprise about 0.5%; about 1.0%; about 1.5%; about 2.0%; about 2.5%; about 3.0%; about 3.5%; about 4.0%; about 4.5%; about 5.0%; about 5.5%; about 6.0%; 6.5%; about 7.0%; about 7.5%; about 8.0%; about 8.5%; about 9.0%; about 9.5%; about 10.0%; about 10.5%; about 11.0%; about 11.5%; about 12.0%; about 12.5%; about 13.0%; about 13.5%; about 14.0%; about 14.5%; about 15.0%; about 15.5%; about 16.0%; 16.5%; about 17.0%; about 17.5%; about 18.0%; about 18.5%; about 19.0%; about 19.5%; or about 20.0% sugar (e.g., sucrose).

The pharmaceutical formulations of the present invention may also comprise one or more surfactant. As used herein, the term "surfactant" means a substance which reduces the surface tension of a fluid in which it is dissolved and/or reduces the interfacial tension between oil and water. Surfactants can be ionic or non-ionic. Exemplary non-ionic surfactants that can be included in the formulations of the present invention include, e.g., alkyl poly(ethylene oxide), alkyl polyglucosides (e.g., octyl glucoside and decyl maltoside), fatty alcohols such as cetyl alcohol and oleyl alcohol, cocamide MEA, cocamide DEA, and cocamide TEA. Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 188, poloxamer 407; polyethylene-polypropylene glycol; or polyethylene glycol (PEG). Polysorbate 20 is also known as TWEEN 20, sorbitan monolaurate and polyoxyethylenesorbitan monolaurate.

The amount of surfactant contained within the pharmaceutical formulations of the present invention may vary depending on the specific properties desired of the formulations, as well as the particular circumstances and purposes for which the formulations are intended to be used. In certain embodiments, the formulations may contain about 0.05% to about 5% surfactant; or about 0.1% to about 0.2% surfactant. For example, the formulations of the present invention may comprise about 0.05%; about 0.06%; about 0.07%; about 0.08%; about 0.09%; about 0.10%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; or about 0.30% surfactant (e.g., polysorbate 20).

The pharmaceutical formulations of the present invention may also comprise one or more buffers. In some embodiments, the buffer has a buffering range that overlaps fully or in part the range of pH 5.5-7.4. In one embodiment, the buffer has a pKa of about 6.0±0.5. In certain embodiments, the buffer comprises a phosphate buffer. In certain embodiments, the phosphate is present at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In certain embodiments, the buffer system comprises histidine at 10 mM±1.5 mM, at a pH of 6.0±0.5.

The pharmaceutical formulations of the present invention may have a pH of from about 5.0 to about 8.0. For example, the formulations of the present invention may have a pH of about 5.0; about 5.2; about 5.4; about 5.6; about 5.8; about 6.0; about 6.2; about 6.4; about 6.6; about 6.8; about 7.0; about 7.2; about 7.4; about 7.6; about 7.8; or about 8.0.

In one particular embodiment, the therapeutic protein is a VEGF Trap protein. Pharmaceutical formulations for the formation of micronized VEGF Trap protein particles may contain from about 10 mg/mL to about 100 mg/mL VEGF Trap protein, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, or about 100 mg/mL VEGF Trap protein. Solutions may contain one or more buffers of from about 5 mM to about 50 mM. In one embodiment, the buffer is about 10 mM phosphate at a pH of about 6±0.5. Solutions may also contain sucrose at a concentration of from about 1% to about 10%. In one embodiment, the solution contains sucrose at about 2% w/w.

In some embodiments, the therapeutic protein solution contains VEGF Trap protein at about 25 mg/mL or about 50 mg/mL in 10 mM phosphate, pH 6.2, 2% sucrose, and optionally 0.1% polysorbate.

The therapeutic protein formulation is then subjected to dispersion and drying to form micronized protein particles. One method of making the micronized protein particles is to subject the protein solution to spray-drying. Spray-drying is generally known in the art and may be performed on equipment such as e.g., a BÜCHI Mini Spray Dryer B-290 (Büchi Labortechnik AG, Flawil, CH). In one particular embodiment, the protein solution (e.g., but not limited to any one of the VEGF Trap formulations described above) is pumped into the spray dryer at a rate of about 2 mL/min to about 15 mL/min, or about 7 mL/min. The inlet temperature of the spray dryer is set at a temperature above the boiling point of water, such as e.g., at about 130° C. The outlet temperature at a temperature below the boiling point of water and above ambient temperature, such as e.g., 55° C. In one specific embodiment, a protein solution (e.g., VEGF Trap solution or IgG solution) is pumped into a BÜCHI Mini Spray Dryer B-290 at about 7 mL/min, with an inlet temperature of about 130° C. and an outlet temperature of about 55° C., with the aspirator set at 33 m³/h and the spray gas at 530 L/h.

The resulting micronized protein particles range in size from about 1 μm to about 100 μm in diameter, depending upon the particular formulation and concentration of protein and excipients. In some embodiments, the micronized protein particles have a diameter of from about 1 μm to about 100 μm, from about 1 μm to about 40 μm, from about 2 μm to about 15 μm, from about 2.5 μm to about 13 μm, from about 3 μm to about 10 μm, about 5 μm, about 6 μm, about 7 μm, about 8 μm, about 9 μm, about 10 μm, about 11 μm, or about 12 μm.

The micronized protein particles are then coated with a biocompatible and biodegradable polymer. This is can be accomplished by suspending the micronized protein particles in a polymer solution. A polymer solution is essentially a polymer dissolved in a solvent. For example, the biocompatible and biodegradable polymer may be dissolved in inter alia methylene chloride, tetrahydrofuran, ethyl acetate, or some other useful solvent. Ethyl acetate is widely known as a safe solvent and is often used in the preparation of drugs, implants and foodstuffs.

In some embodiments, the polymer can be ethyl cellulose ("EC"), poly(lactic acid) ("PLA"), polyorthoester ("POE"), poly-D,L-lactide-co-glycolide ("PLGA"), or poly-ε-caprolactone ("PCL"). The polymer can be dissolved in the solvent (e.g., ethyl acetate) at a concentration of from about 10 mg/mL to about 300 mg/mL, from about 15 mg/mL to about 295 mg/mL, from about 20 mg/mL to about 290 mg/mL, from about 25 mg/mL to about 280 mg/mL, from about 30 mg/mL to about 270 mg/mL, from about 35 mg/mL to about 265 mg/mL, from about 40 mg/mL to about 260 mg/mL, from about 45 mg/mL to about 260 mg/mL, from about 50 mg/mL to about 255 mg/mL, from about 55 mg/mL to about 250 mg/mL, about 20 mg/mL, about 25 mg/mL, about 30 mg/mL, about 35 mg/mL, about 40 mg/mL, about 45 mg/mL, about 50 mg/mL, about 75 mg/mL, about 100 mg/mL, about 125 mg/mL, about 150 mg/mL, about 175 mg/mL, about 200 mg/mL, about 225 mg/mL, or about 250 mg/mL.

The micronized protein particles are added to the polymer solution at about 10 mg/mL to about 100 mg/mL, about 15 mg/mL to about 95 mg/mL, about 20 mg/mL to about 90 mg/mL, about 25 mg/mL to about 85 mg/mL, about 30 mg/mL to about 80 mg/mL, about 35 mg/mL to about 75 mg/mL, about 40 mg/mL to about 70 mg/mL, about 45 mg/mL to about 65 mg/mL, about 50 mg/mL to about 60 mg/mL, at about 25 mg/mL, at about 30 mg/mL, at about 35 mg/mL, at about 40 mg/mL, at about 45 mg/mL, or at about 50 mg/mL. The particles are mixed to form a slurry or suspension, which is then subjected to dispersion and drying to form the polymer coated protein particle (i.e., microparticle).

In one embodiment, the protein particle-polymer solution suspension is subjected the spray-drying, which is performed in a manner similar to the method for manufacturing the micronized protein particles, but with a reduced intake temperature to protect against igniting the organic solvent or polymer. Briefly, the protein particle-polymer solution suspension is pumped into the spray dryer at a rate of about 5 mL/min to about 20 mL/min, or about 12.5 mL/min. The suspension was pumped at 12.5 mL/min into the spray dryer with an aspirator air and spray gas flow rate of about 530 L/h and 35 m³/h (mm), respectively. The inlet temperature was set at 90° and the outlet temperature was set at about 54° C.

The inlet temperature of the spray dryer is set at a temperature above the flash point of the solvent, such as e.g., at about 90° C. The outlet temperature at a temperature below the intake temperature and above ambient temperature, such as e.g., about 54° C. In one particular embodiment, a suspension containing about 50 mg/mL of protein particle (e.g., VEGF Trap) in about 50 mg/mL to about 250 mg/mL polymer/ethyl acetate solution is pumped into a BÜCHI Mini Spray Dryer B-290 at about 12.5 mL/min, with an inlet temperature of about 90° C. and an outlet temperature of about 54° C., with the aspirator set at about 35 m³/h and the spray gas at about 530 L/h.

The resulting microparticles, which contain a protein particle core within a polymer cortex, have a range of diameters of from about 2 μm to about 70 μm, about 5 μm to about 65 μm, about 10 μm to about 60 μm, about 15 μm to about 55 μm, about 20 μm to about 50 μm, about 15 μm, about 20 μm, about 25 μm, or about 30 μm. The size variation in large part reflects the thickness of the polymer cortex, although the diameter of the protein core could contribute to size variation to some extent. Manipulating the starting concentration of the polymer solution, and/or the polymer itself can control the diameter of the microparticle. For example, those microparticles which were manufactured using 50 mg/mL polymer have a median size of about 15 μm to 20 μm, whereas those microparticles which were manufactured using 250 mg/mL polymer had a median size of about 30 μm.

The microparticles of the instant invention are useful in the time-release or extended release of protein therapeutics. For example, it is envisioned that the VEGF Trap microparticles are useful in the extended release of VEGF Trap therapeutic protein in, for example, the vitreous for the treatment of vascular eye disorders, or subcutaneous implantation for the extended release of VEGF Trap to treat cancer or other disorders.

The microparticles of the instant invention release protein in a physiological aqueous environment at about 37° C. at a relatively constant rate over an extended period of time, to at least 60 days. In general, those microparticles manufactured with a higher concentration of polymer (e.g., 250 mg/mL) tended to show a relatively linear protein release profile; whereas those microparticles manufactured with a lower concentration of polymer (e.g., 50 mg/mL) tended to show an initial burst followed by an onset of a delayed burst release. Furthermore, microparticles formed from a higher concentration of polymer showed a slower rate of release of protein than those formed from a lower concentration of particles. The quality of protein released from the microparticles over time was consistent with the quality of the stating protein material. Little to no protein degradation occurred.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, sizes, etc.) but some experimental errors and deviations should be accounted for.

In the following examples, VEGF-Trap protein ("VGT"), which is a dimer of the polypeptide comprising the amino acid sequence SEQ ID NO:1, serves as an exemplar receptor-Fc-fusion protein.

Example 1: Micronized Proteins

Solutions containing 25 mg/mL VEGF Trap protein ("VGT"), 25 mg/mL VGT plus 0.1% polysorbate 80, and 50 mg/mL VGT in 10 mM phosphate, 2% sucrose, pH 6.2 were each independently atomized in a spray dry micronizer (BÜCHI Mini Spray Dryer B-290, Büchi Labortechnik AG, Flawil, CH) to form droplets containing VEGF Trap. Heat was applied to evaporate the water from the droplets, resulting in a powder containing VEGF Trap. The inlet temperature was set at 130° C. and outlet temperature at about 55° C. The aspirator was set at 33 m³/h and spray gas at 530 L/h. The VGT solution was pumped at about 7 mL/min.

The size of the resultant VGT particles was measured by micro-flow imaging (MFI) and dynamic light imaging (DLS). FIG. 1 depicts the particle size distribution as determined by MFI for the VGT particles derived from each of the 25 mg/mL VGT, 25 mg/mL VGT plus 0.1% polysorbate 80, and 50 mg/mL VGT concentrations. For all concentrations, the equivalent circular diameter (ECD) of VGT particles ranged from about 1 μm to about 39 μm, with the majority of particles ranging in size of from about 2 μm to about 14 μm. For the 25 mg/mL VGT solution, the particles clustered in the range of about 2.5 μm to about 8.8 μm, with a mode of about 6 μm. For the 25 mg/mL VGT plus 0.1% polysorbate 80 solution, the particles clustered in the range of about 2.5 μm to about 9.7 μm, with a mode of about 6 μm. For the 50 mg/mL VGT solution, the particles clustered in the range of about 2.7 μm to about 12.8 μm, with a mode of about 7 μm. Median diameters for each formulation, as determined by both MFI and DLS methods, are described in Table 1.

VGT particles were reconstituted in water for injection and examined via size exclusion, i.e., size exclusion-ultra performance liquid chromatography (SE-UPLC) to determine protein purity. No change in purity was noted after micronization relative to starting material (see Table 3).

TABLE 1

Median protein particle sizes (μm) as determined by MFI and DLS

| Formulation | Median size by MFI (μm) | Median size by DLS (μm) |
|---|---|---|
| 50 mg/mL VEGF Trap | 7 | 7.6 |
| 25 mg/mL VEGF Trap | 6 | 5.9 |
| 25 mg/mL VEGF Trap, 0.1% polysorbate 80 | 6 | 7.1 |

Example 2: Micronized Protein Suspensions in Organic Polymer Solutions

Various polymers were used or are contemplated for use in the manufacture of the polymer cortex of the microparticles. Those polymers include inter alia ethyl cellulose ("EC"), polyorthoester ("POE"), poly-D,L-lactide-co-glycolide ("PLGA"), and poly-ε-caprolactone ("PCL").

Ethyl Cellulose Coating

Micronized VEGF Trap particles were suspended in a solution of 50 mg/mL ethyl cellulose in ethyl acetate at a concentration of about 50 mg/mL VGT; herein designated "VGT-50-EC suspension".

Micronized VEGF Trap particles were suspended in a solution of 100 mg/mL ethyl cellulose in ethyl acetate at a concentration of about 50 mg/mL VGT; herein designated "VGT-100-EC suspension".

Micronized VEGF Trap particles are suspended in a solution of 250 mg/mL ethyl cellulose in ethyl acetate at a concentration of about 50 mg/mL VGT; herein designated "VGT-250-EC suspension".

Polyorthoester Coating

Micronized VEGF Trap particles were suspended in a solution of 50 mg/mL polyorthoester containing about 5% latent acid in ethyl acetate at a concentration of about 50 mg/mL VGT; herein designated "VGT-50-POE suspension".

Micronized VEGF Trap particles were suspended in a solution of 250 mg/mL polyorthoester containing about 5% latent acid in ethyl acetate at a concentration of about 50 mg/mL VGT; herein designated "VGT-250-POE suspension".

Poly-D,L-Lactide-Co-Glycolide Coating

Micronized VEGF Trap particles were suspended in a solution of 50 mg/mL PLGA in ethyl acetate at a concentration of about 50 mg/mL VGT; herein designated "VGT-50-PLGA suspension".

Micronized VEGF Trap particles were suspended in a solution of 200 mg/mL PLGA in ethyl acetate at a concentration of about 50 mg/mL VGT; herein designated "VGT-200-PLGA suspension".

Micronized VEGF Trap particles were suspended in a solution of 250 mg/mL PLGA in ethyl acetate at a concentration of about 50 mg/mL VGT; herein designated "VGT-250-PLGA suspension".

Poly-ε-Caprolactone Coating

Micronized VEGF Trap particles are suspended in a solution of 50 mg/mL PCL in ethyl acetate at a concentration of about 50 mg/mL VGT; herein designated "VGT-50-PCL suspension".

Micronized VEGF Trap particles are suspended in a solution of 250 mg/mL PCL in ethyl acetate at a concentration of about 50 mg/mL VGT; herein designated "VGT-250-PCL suspension".

PCL has a low Tg and may not be suitable for heat-drying as described below, but can be used for solvent extraction in an aqueous bath with polyvinyl alcohol (PVA), for example.

Example 3: Dispersion of Protein-Polymer Fine Droplets and Solvent Removal

Each VGT polymer suspension, which was made according to Example 2 (supra), was subjected to spray drying using a BÜCHI Mini Spray Dryer B-290 (Büchi Labortechnik AG, Flawil, CH). Briefly, each suspension was atomized to form microdroplets, which were subsequently heat dried to remove the solvent and form the polymer-coated protein microparticles. The suspension was pumped at 12.5 mL/min into the spray dryer with an aspirator air and spray gas flow rate of about 530 L/h and 35 m$^3$/h, respectively. The inlet temperature was set at 90° and the outlet temperature was set at about 54° C.

Example 4: Characterization of Protein-Polymer Microparticles

Spray dried polymer coated protein particles manufactured according to the exemplified process generate a plurality of microparticles having a range of equivalent circular diameters of from about 2.5 μm to about 65 μm (FIG. 2). The size variation in large part reflects the thickness of the polymer cortex, although the diameter of the protein core could contribute to size variation to some extent.

The diameter of the microparticle correlates with the starting concentration of the polymer solution (Table 2, FIG. 2). Those microparticles which were manufactured using 50 mg/mL polymer had a median size of about 17 μm±2.8 μm. Those microparticles which were manufactured using 250 mg/mL polymer had a median size of about 29 μm.

Example 5: Protein Stability Post Spray Dry

The stability of the VEGF-Trap protein was assessed using quantitative size exclusion chromatography (SE-UPLC), which allows for the quantification of smaller degradation products and larger aggregation products relative to the intact monomer. The results are described in Table 3. Essentially, the protein remained stable throughout the spray drying and spray coating processes.

The average ratio of protein to polymer by weight was also determined for the manufactured microparticles. A collection of microparticles manufactured with varying polymers and polymer concentration was extracted and subjected to quantitative reverse phase chromatography (RP-HPLC). The results are presented in Table 3. The data may be interpreted to support the theory that a higher starting concentration of polymer yields a thicker polymer cortex on the microparticle.

TABLE 2

Equivalent circular diameter values

| Material | Range (μm) | Median (μm) | Mode (μm) |
| --- | --- | --- | --- |
| VEGF-Trap ("VGT") (50 mg/mL) | 2.5-29.4 | 10-12 | 8.3 |
| VGT (50 mg/mL) + POE (50 mg/mL) | 2.5-64.5 | 15 | 9.4 |
| VGT (50 mg/mL) + POE (250 mg/mL) | 2.5-49.4 | 29 | 28.5 |
| VGT (50 mg/mL) + EC (50 mg/mL) | 2.5-49.6 | 19 | 16.5 |

TABLE 3

Protein stability and loading

| Material | VGT starting material % Native | VGT Extracted from Coated Polymers[1] | |
| --- | --- | --- | --- |
| | | % Native[2] | % w/w VGT/polymer[3] |
| VGT starting material | 97.7 | — | — |
| Reconstituted VGT | 97.6 | — | — |
| VGT (50 mg/mL) + POE (50 mg/mL) | — | 96.3 | 14.6 |
| VGT (50 mg/mL) + POE (250 mg/mL) | — | 97.7 | 1.8 |
| VGT (50 mg/mL) + EC (50 mg/mL) | — | 97.1 | 6.1 |

[1]Based on extracted VEGF Trap after 1 hour reconstitution to remove uncoated VEGF Trap.
[2]Average of percent native by SE-UPLC (n = 4).
[3]Average of percent weight to weight loading of VGT to polymer by RP-HPLC (n = 4).

Example 6: Protein Release from Microparticles

The release of protein from microparticles was determined by suspending various batches of microparticles in buffer (10 mM phosphate, 0.03% polysorbate 20, pH 7.0) and measuring the amount and quality of protein released into solution over time while incubated at 37° C. At 1-2 week intervals, the microparticles were pelleted by mild centrifugation and 80% of the supernatant containing released protein was collected for subsequent analysis. An equivalent amount of fresh buffer was replaced and the microparticles were resuspended by mild vortexing and returned to the 37° C. incubation chamber. Protein amount and quality in the supernatant was assessed by size exclusion chromatography.

In general, those microparticles manufactured with a higher concentration of polymer (e.g., 250 mg/mL) tended to show a relatively linear protein release profile; whereas those microparticles manufactured with a lower concentration of polymer (e.g., 50 mg/mL) tended to show an initial burst followed by an onset of a delayed burst release. The data showing the extended release of protein, which remained stable, for up to about 60 days is depicted in FIG. 3 (release data). Table 4 summarizes the linear rate-of-release data.

TABLE 4

Protein release dynamics

| Material | VEGF Trap protein release (mg VGT/week) |
| --- | --- |
| VGT (50 mg/mL) + POE (50 mg/mL) | 0.14 ± 0.16 |
| VGT (50 mg/mL) + POE (250 mg/mL) | 0.06 ± 0.02 |
| VGT (50 mg/mL) + EC (50 mg/mL) | 0.031 ± 0.02 |

Example 7: Particle Size can be Manipulated by Polymer Concentration and Spray Gas Flow Particle size distributions were controlled by polymer concentration and atomization spray gas flow. Increased polymer concentration shifted the distribution towards larger particles (200 mg/mL PLGA at 45 mm spray gas flow v. 100 mg/mL PLGA at 45 mm spray gas flow; see Table 5). Similarly, a lower atomization spray gas flow resulted in larger droplets and thus, larger particles (100 mg/mL PLGA at 25 mm spray gas flow v. 100 mg/mL PLGA at 45 mm spray gas flow; see Table 5).

TABLE 5

Particle Size (all metrics are approximate)

| [PLGA] (mg/mL) | Gas Flow Rate ($m^3/h$) | Particle size range (microns) | Mode of particle size (microns) | Percent total volume of particles with 15 micron particle size |
| --- | --- | --- | --- | --- |
| Protein alone | NA | 2.5-25 | 3.5 | 1.5% |
| 100 | 25 | 2.5-40 | 9.4 | 3.7% |
| 100 | 45 | 2.5-30 | 9.4 | 3.7% |
| 200 | 45 | 2.5-30 | 10.2-15.4 | 5.4% |

Example 8: Particle Size and Protein Release Across Various Polymers

VEGF Trap or IgG was spray coated with low molecular weight (202S) poly(lactic acid) (PLA-LMW), high molecular weight (203S) poly(lactic acid) (PLA-HMW), polyanhydride poly[1,6-bis(p-carboxyphenoxy)hexane] (pCPH), poly(hydroxybutyric acid-cohydroxyvaleric acid) (PHB-PVA), PEG-poly(lactic acid) block copolymer (PEG-PLA), and poly-D,L-lactide-co-glycolide (PLGA). 25 mg/mL of spray-dried protein was combined with 50-100 mg/mL polymer. In vitro release assays were performed in 10 mM phosphate buffer, pH7.2 at 37° C. The results are depicted in Table 6.

TABLE 6

Polymer dependent particle size and protein release (all metrics are approximate)

| Polymer | Protein | Relative number of particles at 15 microns | Time to 100% protein release |
| --- | --- | --- | --- |
| PLA-LMW | VEGF Trap | $0.8 \times 10^2$ | 3 days |
| PLA-HMW | VEGF Trap | $0.8 \times 10^2$ | 3 days |
| pCPH | VEGF Trap | $1 \times 10^2$ | 3 days |
| PHB-PVA | VEGF Trap | $5 \times 10^2$ | 1 days |
| PEG-PLA | VEGF Trap | $0.6 \times 10^2$ | 6 hours |
| PLGA | IgG | $1 \times 10^2$ | 8 days |

Example 9: Protein Stability in Various Polymers

VEGF Trap and IgG were extracted from their respective polymer coats and measured for purity by SE-UPLC. The results are summarized in Table 7. The proteins generally were compatible with the spray coating process for the polymers tested. Protein remained stable for at least 14 days for those polymers that continued to release protein.

TABLE 7

% Purity by Size Exclusion Chromatography

| Protein | Polymer | After spray coating | 1 day in vitro release (IVR) | 3 days IVR | 14 days IVR |
| --- | --- | --- | --- | --- | --- |
| VEGF Trap | POE (AP141) | 97.7 | 98.3 | 98.2 | 96.7 |
| VEGF Trap | PLA-LMW | 97.0 | 97.4 | 92.8 | — |
| VEGF Trap | PLA-HMW | 93.9 | 97.3 | 95.4 | — |
| VEGF Trap | PEG-PLA | 89.9 | 91.2 | — | — |
| VEGF Trap | pCPH | 89.2 | 94.2 | 84.8 | — |
| VEGF Trap | PHB-PVA | 97.4 | 96.2 | — | — |
| VEGF Trap | PLGA | 96.6 | 97.8 | — | 93.6 |
| IgG | PLGA | 99.2 | 98.0 | — | 92.0 |

What is claimed is:

1. A method of manufacturing an extended release pharmaceutical composition comprising therapeutic protein microparticles coated with a biodegradable polymer, the method comprising:
   a. spray drying an aqueous therapeutic protein solution to form therapeutic protein microparticles wherein the inlet temperature of the spray dryer is set at a temperature greater than the boiling point of water and the outlet temperature that is above ambient and below the boiling point of water to form a powder comprising a population of therapeutic protein microparticles wherein the aqueous solution is pumped into the spray dryer at a rate of 2 mL/min to 15 mL/min,
   b. suspending the powder comprising the population of therapeutic protein microparticles in a solution comprising polyorthoester (POE) and an organic solvent to form a suspension; and
   c. spray drying the suspension to form the extended release pharmaceutical composition comprising a population of POE-coated therapeutic protein microparticles, wherein the extended release pharmaceutical composition comprises about 1 to about 500 mg/mL of therapeutic protein microparticles and releases the therapeutic protein for at least 60 days at a steady rate of release, wherein extended release pharmaceutical composition can treat conditions selected from the group consisting of cancers, cardiovascular diseases, vascular conditions, orthopedic disorders, dental disorders, wounds, autoimmune diseases, gastrointestinal disorders and ocular diseases.

2. The method of claim 1, wherein the outlet temperature is about 54 to 55° C.

3. The method of claim 2, wherein each therapeutic protein microparticle of the population of therapeutic protein microparticles comprises less than 3% (w/w) water.

4. The method of claim 1, wherein the organic solvent is ethyl acetate.

5. The method of claim 1, wherein the spray drying the suspension (c) comprises atomizing the suspension and then applying heat to the atomized suspension at a temperature greater than the flash point of the organic solvent to evaporate the organic solvent to form the population of POE-coated therapeutic protein microparticles.

6. The method of claim 5, wherein the median diameter of the population of POE-coated therapeutic protein microparticles is about 15 microns to about 30 microns.

7. The method of claim 1, wherein each therapeutic protein microparticle of the population of therapeutic protein microparticles has a diameter of about 2 microns to about 14 microns.

8. The method of claim 1, wherein the condition is cancer.

9. The method of claim 1, wherein the condition is cardiovascular disease.

10. The method of claim 1, wherein the condition is a vascular disorder.

11. The method of claim 1, wherein the condition is a wound.

12. The method of claim 1, wherein the condition is an autoimmune disease.

13. The method of claim 1, wherein the condition is an orthopedic disorder.

14. The method of claim 1, wherein the condition is a gastrointestinal disorder.

15. The method of claim 1, wherein the condition is an ocular disease.

16. A method of providing an extended release coating for therapeutic protein comprising:
   a. atomizing an aqueous solution comprising a therapeutic protein;
   b. spray drying the atomized aqueous solution at a temperature greater than the boiling point of water to remove water in the solution and form a population of therapeutic protein microparticles;
   c. coating each therapeutic protein microparticle of the population therapeutic protein microparticles with a biodegradable polymer to form a population of polymer-coated therapeutic protein microparticles, wherein the biodegradable polymer is polyorthoester,
   wherein the extended release pharmaceutical composition releases the therapeutic protein for at least 60 days at a steady rate of release, wherein extended release pharmaceutical composition can treat conditions selected from the group consisting of cancers, cardiovascular diseases, vascular conditions, orthopedic disorders, dental disorders, wounds, autoimmune diseases, gastrointestinal disorders and ocular diseases.

17. The method of claim 16, wherein the population of therapeutic protein microparticles is dry.

18. The method of claim 16, wherein the population of therapeutic protein microparticles comprises less than 3% water.

19. The method of claim 16, wherein the aqueous solution comprises about 10 mg/mL to 100 mg/mL of the therapeutic protein.

20. The method of claim 16, wherein the coating step (c) further comprises:
   combining: (1) an organic solvent with the biodegradable polymer to a concentration of between about 10 mg/mL and 300 mg/mL; and (2) the population of therapeutic protein microparticles to a concentration of between about 10 mg/mL and 100 mg/mL to form a slurry; and spray drying the slurry to form the plurality of polymer-coated therapeutic protein microparticles at step (c).

* * * * *